United States Patent
Wei et al.

(10) Patent No.: US 11,394,129 B2
(45) Date of Patent: Jul. 19, 2022

(54) MULTIPLE BAND ANTENNA STRUCTURES

(71) Applicant: Fitbit, Inc., San Francisco, CA (US)

(72) Inventors: Yonghua Wei, San Diego, CA (US); Faton Tefiku, San Diego, CA (US); Christos Kinezos Ioannou, San Diego, CA (US); Kevin Li, San Diego, CA (US)

(73) Assignee: FITBIT, INC., San Francisco, CA (US)

( * ) Notice: Subject to any disclaimer, the term of this patent is extended or adjusted under 35 U.S.C. 154(b) by 15 days.

(21) Appl. No.: 16/682,257

(22) Filed: Nov. 13, 2019

(65) Prior Publication Data

US 2020/0194905 A1 Jun. 18, 2020

Related U.S. Application Data

(60) Provisional application No. 62/779,093, filed on Dec. 13, 2018.

(51) Int. Cl.
*H01Q 1/24* (2006.01)
*H01Q 21/30* (2006.01)
(Continued)

(52) U.S. Cl.
CPC ........ *H01Q 21/30* (2013.01); *A61B 5/0006* (2013.01); *A61B 5/1112* (2013.01);
(Continued)

(58) Field of Classification Search
CPC ......... H01Q 1/243; H01Q 1/273; H01Q 1/38; H01Q 1/48; H01Q 5/371; H01Q 7/00; H01Q 9/0407; H01Q 9/42; H01Q 13/18; H01Q 13/16; H01Q 1/526; H01Q 21/30; H04W 4/80; H04W 64/00; H04W 24/08; H04W 12/068; H04W 4/70; H04W 52/0254; H04W 4/026
(Continued)

(56) References Cited

U.S. PATENT DOCUMENTS 7,558,057 B1   7/2009 Naksen
9,391,307 B2   7/2016 Ishibashi
(Continued)

OTHER PUBLICATIONS

Notice of Allowance issued in U.S. Appl. No. 16/682,280 dated Sep. 21, 2020.
(Continued)

*Primary Examiner* — Linh V Nguyen
(74) *Attorney, Agent, or Firm* — Dority & Manning, P.A.

(57) ABSTRACT

Various antenna designs are presented that can be used to provide for wireless communication in electronic devices, such as wearable electronic devices. Various embodiments provide antenna structures and designs that can support multiple frequency bands in a relatively compact space. Various embodiments utilize a slot and patch antenna design to support multiple frequency bands. Other embodiments utilize a slot and inverted "F" antenna (IFA) assembly, hybrid slot antenna assembly, or external slot antenna assembly. A split ring antenna assembly can also be used, where individual segments of the ring antenna can support specific frequency bands. Other embodiments utilize a dielectrically loaded planar inverted "F" antenna (PIFA) assembly to support various frequency bands.

20 Claims, 14 Drawing Sheets

(51) Int. Cl.

| | |
|---|---|
| *H01Q 13/18* | (2006.01) |
| *H01Q 13/16* | (2006.01) |
| *H01Q 9/04* | (2006.01) |
| *H01Q 1/27* | (2006.01) |
| *H04W 4/80* | (2018.01) |
| *A61B 5/00* | (2006.01) |
| *A61B 5/11* | (2006.01) |
| *G06F 1/16* | (2006.01) |
| *H01Q 1/38* | (2006.01) |
| *H01Q 1/48* | (2006.01) |
| *H01Q 1/52* | (2006.01) |
| *H01Q 7/00* | (2006.01) |

(52) U.S. Cl.
CPC ............ *A61B 5/1118* (2013.01); *A61B 5/681* (2013.01); *G06F 1/163* (2013.01); *H01Q 1/273* (2013.01); *H01Q 1/38* (2013.01); *H01Q 1/48* (2013.01); *H01Q 1/526* (2013.01); *H01Q 7/00* (2013.01); *H01Q 9/0421* (2013.01); *H01Q 13/16* (2013.01); *H01Q 13/18* (2013.01); *H04W 4/80* (2018.02)

(58) Field of Classification Search
USPC .................... 343/718, 747, 767, 769, 702
See application file for complete search history.

(56) References Cited

U.S. PATENT DOCUMENTS

| | | | |
|---|---|---|---|
| 9,442,523 B2 | 9/2016 | Lee | |
| 9,529,396 B2 | 12/2016 | Shen | |
| 9,760,064 B2 | 9/2017 | Kim | |
| 9,760,115 B2 | 9/2017 | Farjami | |
| 9,760,119 B2 | 9/2017 | Hung | |
| 9,874,901 B2 | 1/2018 | Seok | |
| 10,016,161 B2 | 7/2018 | Townsend | |
| 10,114,414 B2 | 10/2018 | Lee | |
| 10,271,299 B1* | 4/2019 | Sayem | H01Q 1/50 |
| 10,289,158 B2 | 5/2019 | Hiraki | |
| 10,338,638 B2 | 7/2019 | Park | |
| 10,355,344 B1* | 7/2019 | Ruaro | H04B 1/40 |
| 10,484,958 B2 | 11/2019 | Sayem | |
| 10,545,536 B2* | 1/2020 | Rider | G06F 1/163 |
| 10,691,167 B2* | 6/2020 | Lin | G06F 1/1652 |
| 2014/0015719 A1* | 1/2014 | Ramachandran | H01Q 5/50 |
| | | | 343/745 |
| 2014/0266920 A1 | 9/2014 | Tran | |
| 2016/0056533 A1 | 2/2016 | Nissinen | |
| 2016/0209513 A1 | 7/2016 | Hirahama | |
| 2016/0313769 A1* | 10/2016 | Yoshitani | G09G 3/3611 |
| 2017/0179581 A1 | 6/2017 | Puuri | |
| 2018/0034135 A1 | 2/2018 | Kwak | |
| 2018/0048058 A1* | 2/2018 | Ehman | H04B 5/0031 |
| 2018/0069300 A1 | 3/2018 | Choi | |
| 2018/0083342 A1* | 3/2018 | Lepe | H01Q 1/243 |
| 2018/0129170 A1* | 5/2018 | Yun | G04G 17/045 |
| 2018/0166772 A1 | 6/2018 | Wei | |
| 2018/0269561 A1 | 9/2018 | Kim | |
| 2019/0067803 A1 | 2/2019 | Kang | |
| 2019/0081396 A1 | 3/2019 | Zhou | |
| 2019/0131696 A1* | 5/2019 | Hanshew | H01Q 21/28 |
| 2019/0245272 A1* | 8/2019 | Varjonen | G04R 60/06 |
| 2019/0319339 A1 | 10/2019 | Wen | |
| 2019/0372205 A1* | 12/2019 | Ruaro | H01Q 13/10 |

OTHER PUBLICATIONS

Non-Final Office Action issued in U.S. Appl. No. 16/986,078 dated Sep. 22, 2020.
Notice of Allowance issued in U.S. Appl. No. 16/986,078 dated Jan. 12, 2021.
Non-Final Office Action issued in U.S. Appl. No. 16/682,267 dated Dec. 24, 2020.

* cited by examiner

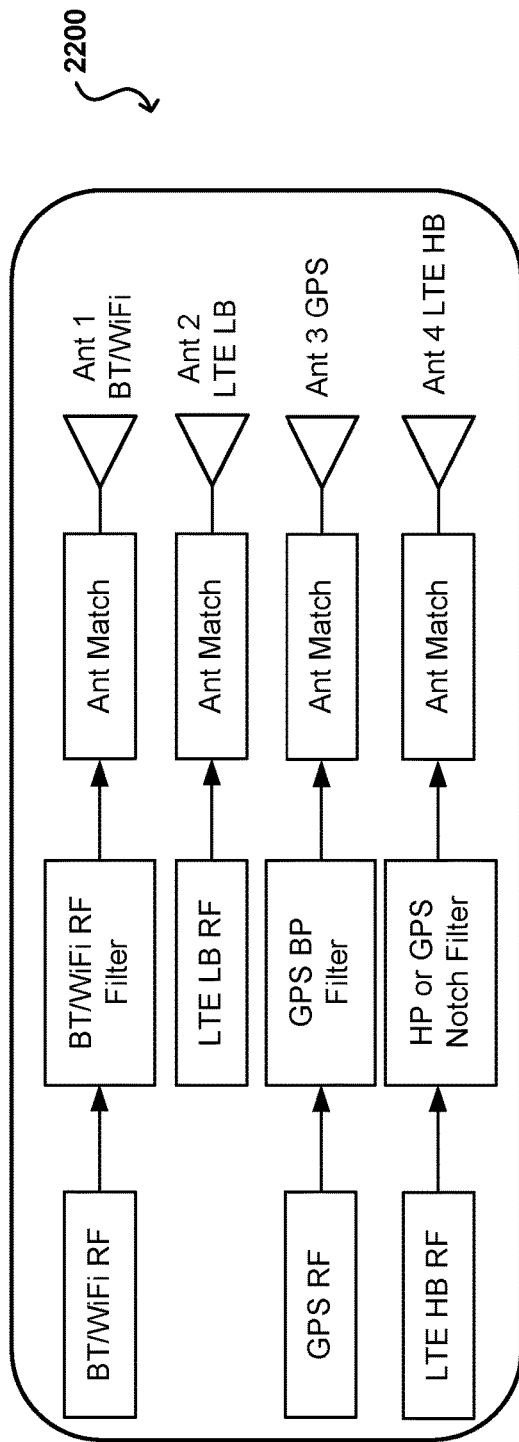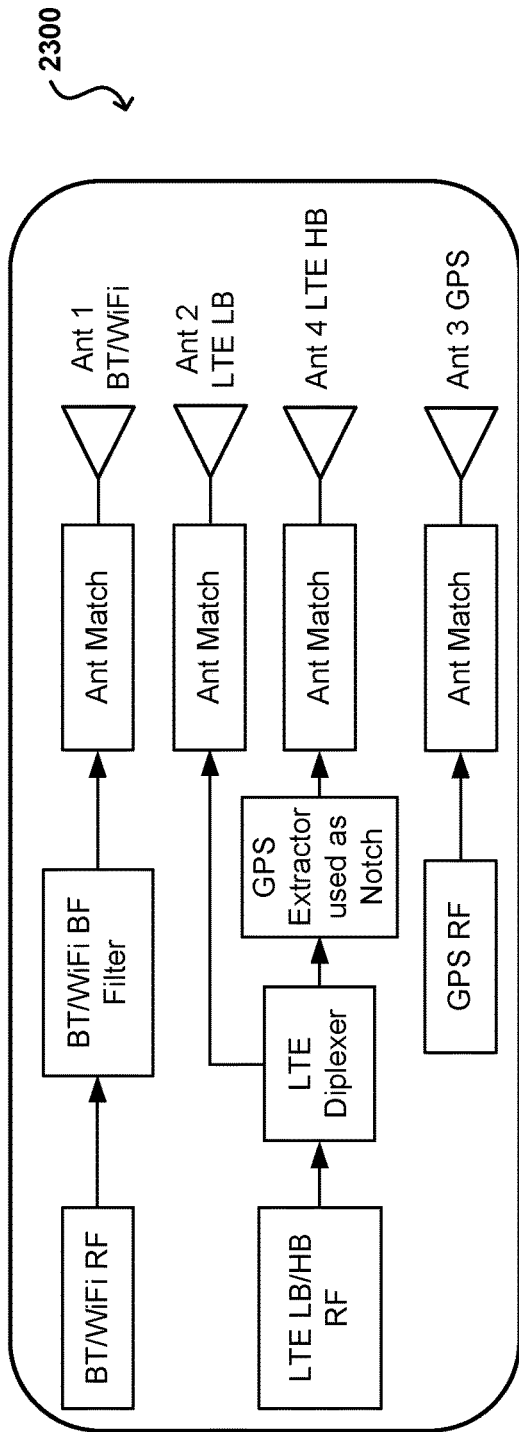
FIG. 22
FIG. 23

MULTIPLE BAND ANTENNA STRUCTURES

CROSS-REFERENCE TO RELATED APPLICATION

This application claims priority to U.S. Provisional Application 62/779,093, filed Dec. 13, 2018, entitled "MULTIPLE BAND ANTENNA STRUCTURES," which is hereby incorporated herein by reference for all purposes.

BACKGROUND

Modern electronic devices frequently include one or more radio-frequency (RF) antennas to facilitate wireless communication with other electronic devices. For example, in small wearable electronic devices the antennas may be configured to fit within a restricted space while still providing desirable emission and reception characteristics. It can be desirable for these devices to support multiple wireless communication bands, but the restricted space makes the successful inclusion and operation of all necessary components challenging.

BRIEF DESCRIPTION OF THE DRAWINGS

Various embodiments in accordance with the present disclosure will be described with reference to the drawings, in which:

FIG. 22 illustrates a first circuit schematic for use with a split ring antenna assembly in accordance with various embodiments.

FIG. 23 illustrates a second circuit schematic for use with a split ring antenna assembly in accordance with various embodiments.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Approaches in accordance with various embodiments provide for wireless communication in electronic devices, such as wearable electronic devices. In particular, various embodiments provide antenna structures and designs that can support multiple frequency bands (e.g., radio frequency (RF) bands) in a relatively compact space. Various embodiments utilize a slot and patch antenna design to support multiple frequency bands. Other embodiments utilize a slot and inverted "F" antenna (IFA) assembly, hybrid slot antenna assembly, or external slot antenna assembly. A split ring antenna assembly can also be used, where individual segments of the ring antenna can support specific frequency bands. Other embodiments utilize a dielectrically loaded planar inverted "F" antenna (PIFA) assembly to support various frequency bands.

Various other aspects and functions can be implemented within the various embodiments as well as discussed and suggested elsewhere herein.

Figure 1:
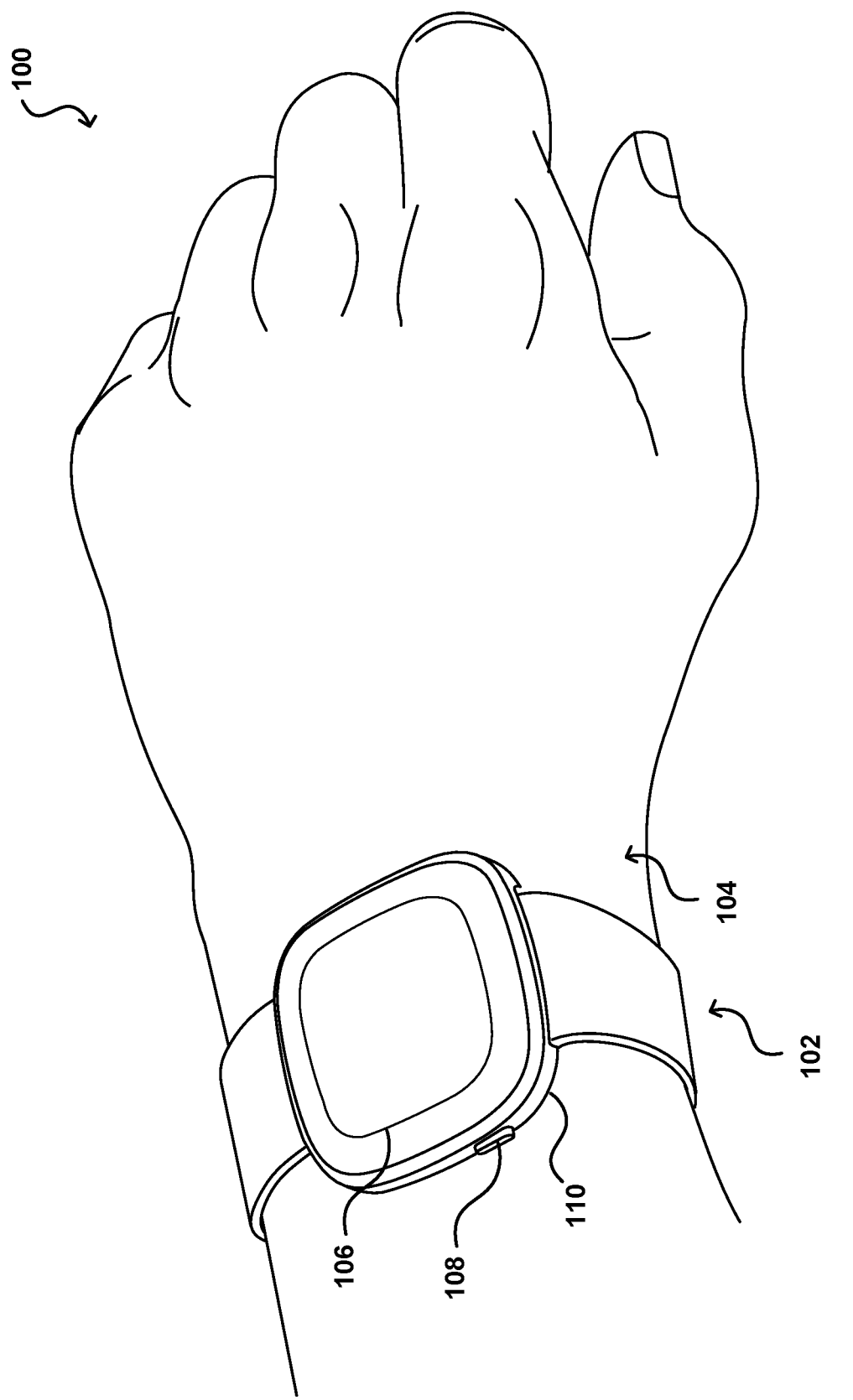
FIG. 1 illustrates an example wearable electronic device that can be utilized to implement aspects of the various embodiments.

FIG. 1 illustrates a view 100 of an example electronic device 102 being worn on the arm 104 of a user. Electronic devices, such as wearable electronic devices, can interact with a user through a touch-sensitive display 106, one or more mechanical buttons 108, or other such input mechanisms known for such purposes. Such devices can also be configured to communicate wirelessly with another computing device, such as a smartphone owned by the user wearing the electronic device. While a device such as a smartwatch or fitness tracker is shown, it should be understood that various other types of electronic devices can benefit from advantages of the various embodiments as discussed and suggested herein, and as would be apparent to one or ordinary skill in the art in light of the present disclosure.

Figure 26:
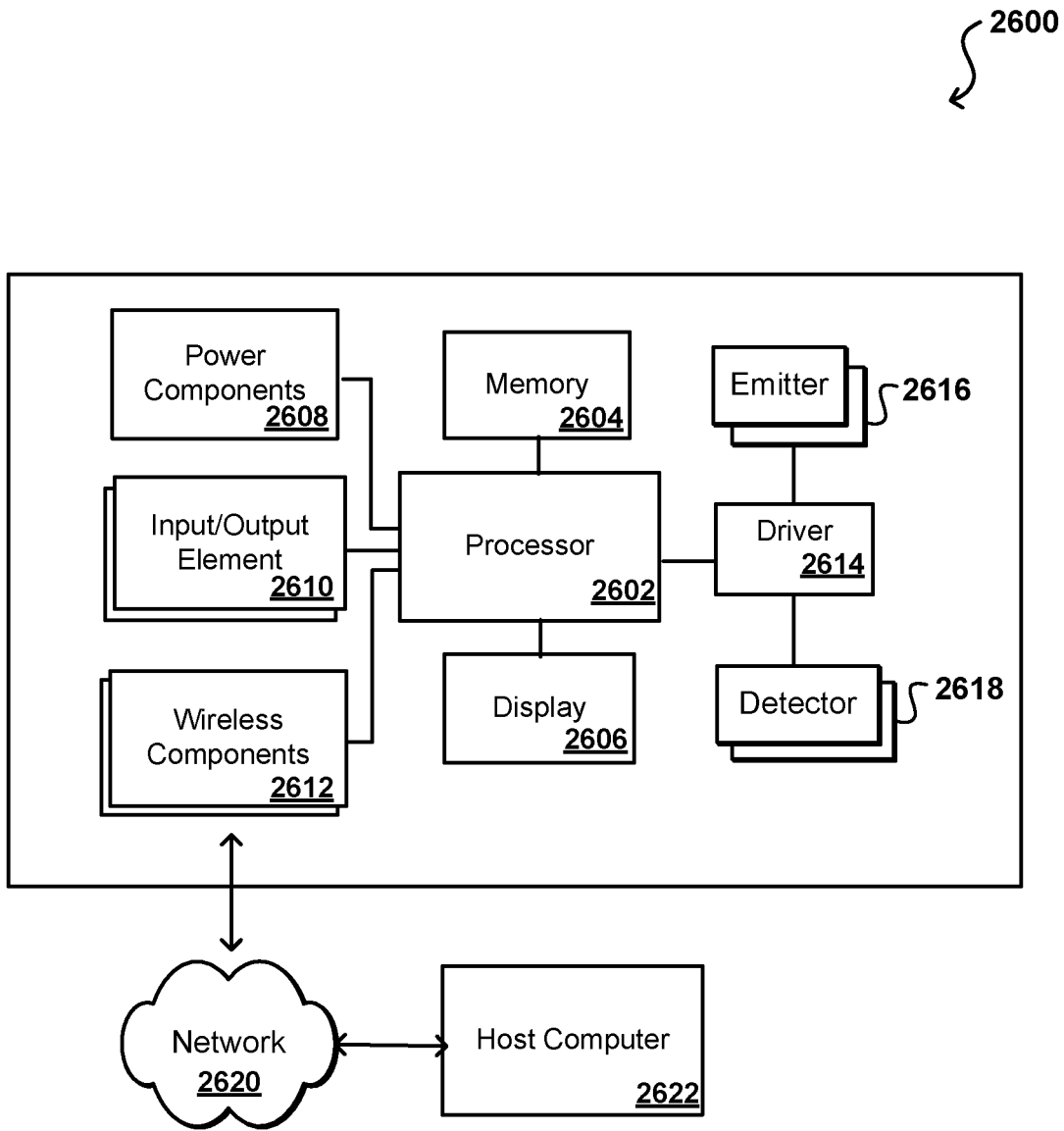
FIG. 26 illustrates components of an example computing environment that can be utilized in accordance with various embodiments.

An example electronic device 102 in accordance with various embodiments can be configured to send and receive data to, and from, one or more separate electronic devices (as illustrated, for example, in FIG. 26). To wirelessly send and receive data, such monitoring devices can utilize one or more antenna elements or assemblies. This may present a variety of problems, as use of a conventional antenna element may result in dead bands, or non-active areas, in a display window of the device. The antenna may occupy significant space within the device housing 110, which may be made of a metal (e.g., stainless steel, aluminum or copper) or other conductive material, or may result in a configuration that negatively impacts the space for other components, such as may relate to a power source, power cell, and/or battery. A reduction in size can result in a corresponding reduction in battery life of the device. Some antennas may be at least partially located outside of the housing 110, which can make it difficult, costly, or otherwise impractical to make the device water resistant. Some antenna designs exert an upward or outward force on the display window, causing the display window to separate from the metal housing over time and no longer be water resistant. Finally, some antenna designs may be undesirably mechanically complex and/or costly. Accordingly, disclosed herein are embodiments of electronic devices, and assemblies for those devices, that address one or more of the above issues while simultaneously supporting wireless communication over multiple communication bands.

Various embodiments discussed herein include two or more antenna structures, or hybrid antenna structures, that include at least one slot antenna. A slot antenna structure can include at least two portions. First, an example structure can include a monopole antenna having a monopole radiator on a plastic carrier implemented at a top of a display area within a metal housing of the device. The monopole radiator is connected through an antenna clip on a printed circuit board (PCB) to a radio frequency (RF) engine. The monopole antenna can be implemented as a flex film antenna radiator assembled on, for example, a plastic carrier. The monopole radiator can generate electromagnetic fields to induce the slot antenna to transmit or receive radio frequency signals.

The slot antenna can be designed to be particularly receptive to (or emissive of) radio frequency (RF) energy at frequencies within the frequency band(s) for the wireless communications protocol(s) that the antenna is designed to support, and the antenna can also be designed to not be particularly receptive to (or emissive of) RF energy at frequencies outside of those frequency band(s). Antennas may achieve such selectivity by virtue of their physical geometry and the dimensions that define that geometry.

As a second portion, a slot antenna structure includes a slot antenna formed by a gap between, for example, a conductive plate and a metal device housing. The slot antenna radiates RF signals from the slot structure through, for example, a display module, a touch module, and/or a glass window. Monopole-excited slot antennas in some embodiments function using a capacitively-coupled monopole antenna radiator to excite an antenna slot. In other embodiments a device can use a slot antenna with a direct feed from a PCB to excite the slot antenna. For a monopole assembly, the monopole radiator and slot antenna are capacitively coupled such that the monopole radiator generates a varying electric field that induces varying electric fields at the slot antenna, resulting in the emission of RF signals. This coupling of electric fields between the monopole radiator and the slot antenna allows for RF signals to be transmitted from and received by the device. The monopole radiator is positioned within the slot area to excite the slot antenna through electromagnetic field coupling. The dimensions of the slot antenna and monopole antenna can be tuned to achieve targeted communication frequency bands. Furthermore, the monopole antenna portion can be tuned to have a certain length and a matching circuit on the PCB may be utilized to tune the antenna impedance to achieve targeted performance characteristics. In some embodiments, the metal plate and/or metal housing can be conductive. The metal plate and/or metal housing can include one or more materials that include a conductivity of 1E5 Siemens/m and/or higher.

Monopole-excited slot antennas can reduce the dead band of the display window or provide a desirably or advantageously small dead band at a top of the display window. The monopole antenna component that excites the slot antenna can provide a targeted excitation for the slot antenna with a reduced distance between a top side of the metal housing and a display module relative to a pure monopole antenna or inverted-F antenna (IFA) architecture with similar antenna performance. In some embodiments, monopole-excited slot antennas accommodate a device architecture having a printed circuit board (PCB) mounted close to the bottom of a metal housing. For tapered metal housings, this allows a relatively large battery to be placed above the PCB and within the metal housing. In contrast, devices with similar tapered metal housings employing other antenna designs may require the PCB to be mounted above the battery to achieve suitable performance, manufacturing costs, and/or mechanical complexity. In such devices, the battery size is reduced relative to devices that incorporate the antenna architectures disclosed herein that allow the battery to be placed above the PCB.

In some embodiments, monopole-excited slot antenna designs can reside entirely within the metal housing. Advantageously, this facilitates manufacturing the device to be water resistant and/or swim proof. Where at least some portion of the antenna is exterior to the metal housing, vias or holes in the metal housing may be required to send and receive electrical signals to the portion of the antenna outside of the metal housing, which may compromise any water-tight capabilities of the device. In some embodiments, monopole-excited slot antenna designs exert no contact pressure force on a glass window or display element of the device. Advantageously, this facilitates manufacturing the device to be water resistant, creating water-tight seals for junctions between components. Where an antenna exerts an outward force on the display window, for example, the display window may tend to separate from the metal housing, compromising the water-tight seal.

The various implementations discussed herein may be used, for example, to provide a slot antenna that provides BLUETOOTH® functionality, including BLUETOOTH Low Energy (Bluetooth LE or BTLE) functionality. Such a compact and efficient antenna may be of particular use in highly-integrated devices having a small form factor. For example, the disclosed antennas can be used in biometric monitoring devices, e.g., wearable devices that track, report, and communicate various biometric measurements, e.g., distance traveled, steps taken, flights of stairs climbed, etc. Such devices may take the form of a small device that is clipped to a person's clothing or worn on a person's wrist. Such a device may, for example, contain various processors, printed circuit boards, sensors, triaxial accelerometers, tri-axial gyroscopes, an altimeter, a display, a vibramotor, a rechargeable battery, a recharging connector, and an input button all within a metal housing that measures approximately between 1.62" and 2" in length, 0.75" and 0.85" in width, and 0.3" and 0.44" in thickness. A monopole-excited slot antenna may be used in such a device to provide RF communication in a water resistant and/or swim-proof wearable device, to reduce the dead band of a display window, and/or to provide a more cost-efficient and mechanically simple device.

Due to the small size of such devices, monopole-excited slot antennas, such as those disclosed herein, may provide the ability to offer a more compact communications solution than might otherwise be possible, allowing additional volume within the metal housing to be made available for other purposes, such as a larger battery. Such dimensions may prove to be particularly well-suited to RF communications in the BLUETOOTH® wireless protocol bands, e.g., 2402 MHz to 2480 MHz.

Slot antenna assemblies that support other wireless communications protocols may also be designed using principles outlined herein. For example, the disclosed antenna architectures may be configured or dimensioned to be suitable for use with wireless networks and radio technologies, such as wireless wide area network (WWAN) (e.g., cellular) and/or wireless local area network (WLAN) carriers. Examples of such wireless networks and radio technologies include but are not limited to Long Term Evolution (LTE) frequency bands or other cellular communications protocol bands, GPS (Global Positioning System) or GNSS (Global Navigation Satellite System) frequency bands, ANT™, 802.11, and ZigBee™, for example, as well as frequency bands associated with other communications standards. The RF radiator size, gaps between components, and other parameters discussed herein may be adjusted as needed in order to produce a monopole-excited slot antenna, as described herein, that is compatible with such other frequency bands.

In some implementations, the wireless devices may provide for at least some type of biometric monitoring. The term "biometric monitoring device" is used herein according to its broad and ordinary meaning, and may be used in various contexts herein to refer to any type of biometric tracking devices, personal health monitoring devices, portable monitoring devices, portable biometric monitoring devices, or the like. In some embodiments, biometric monitoring devices in accordance with the present disclosure may be wearable devices, such as may be designed to be worn (e.g., continuously) by a person (i.e., "user", "wearer", etc.). When worn, such biometric monitoring devices may be configured to gather data regarding activities performed by the wearer, or regarding the wearer's physiological state. Such data may include data representative of the ambient environment around the wearer or the wearer's interaction with the environment. For example, the data may comprise motion data regarding the wearer's movements, ambient light, ambient noise, air quality, etc., and/or physiological data obtained by measuring various physiological characteristics of the wearer, such as heart rate, perspiration levels, and the like.

In some cases, a biometric monitoring device may leverage other devices external to the biometric monitoring device, such as an external heart rate monitor in the form of an EKG sensor for obtaining heart rate data, or a GPS or GNSS receiver in a smartphone may be used to obtain position data, for example. In such cases, the biometric monitoring device may communicate with these external devices using wired or wireless communications connections. The concepts disclosed and discussed herein may be applied to both stand-alone biometric monitoring devices as well as biometric monitoring devices that leverage sensors or functionality provided in external devices, e.g., external sensors, sensors or functionality provided by smartphones, etc.

In an example electronic device utilizing a slot antenna, the device includes a conductive plate within a conductive housing forming a slot antenna. In this example the antenna is excited by a monopole antenna, but other excitement mechanisms can be used as well as discussed elsewhere herein. The housing (such as a metal housing) may be designed to accommodate a display that will be worn on a person's wrist. A wristband may be connected to the opposing ends of the metal housing, and the completed unit may be worn on someone's wrist. The metal housing may be designed to conform better to the cross-sectional curvature of a person's forearm and the interior of the metal housing may be occupied by various electrical components, including a PCB or FPCB (Flexible Printed Circuit Board) that includes, for example, various sensors, processors, power management components, etc. The metal housing may include additional features, such as a metal button bracket, to support other elements within the metal housing.

The slot antenna is structured as a gap between the metal plate and the metal housing (including the metal button bracket) stopped at two ends with grounding contacts between the metal plate and the metal housing. The gap between the metal plate and the metal housing, running between the grounding contacts, forms the slot antenna that, when excited by the monopole antenna, radiates or receives RF signals. The slot antenna can be configured as a half-wavelength slot antenna (e.g., a length of about 6.25 cm for BLUETOOTH® communication). The slot antenna is not directly driven by any element (e.g., an antenna feed or coaxial cable) coupled to the printed circuit board or other similar component. The example slot antenna includes two slot antenna groundings between the metal plate and the metal housing. A third grounding pin can be included to improve performance in some embodiments. The groundings can be used to tune the slot resonance of the slot antenna (e.g., to resonate within the BLUETOOTH® band). The third grounding pin can be used for reducing or preventing unwanted resonances in the remaining gap between the metal housing and the metal plate that may reduce the radiation efficiency of the slot antenna. The grounding clips can be configured as a spring contact or other type of electrical connection. The grounding clips can include elements that terminate in a leaf spring that presses against the metal housing or metal button bracket.

If a monopole design is used, the monopole antenna can be designed to excite the slot antenna in a targeted mode. The monopole antenna includes a flex antenna as the monopole radiator on a monopole antenna carrier made of a plastic mechanical component. The flex antenna is assembled on the surface of the carrier and the carrier is placed inside the metal housing. The carrier can be attached to the metal housing or other component of the device.

In some embodiments a display element can be overlaying at least a portion of the components of the device. The slot antenna can be positioned under a display window of the display element. The slot antenna can then radiate through the window. In some embodiments, and merely by way of example, the display window can be, according to some embodiments, between about 0.65"×1.05" (16.5 mm×26.6 mm) to about 0.77"×1.28" (19.6 mm×32.6 mm).

As mentioned, there may be various frequency bands to be supported in such a device for different types of wireless communication. This can include frequency bands supporting communication protocols such as Long-Term Evolution (LTE) communications, low-power wide-area network (LPWA) air interfaces such as LTE Cat-M1, Global Navigation Satellite System (GNSS), BLUETOOTH, Wi-Fi, and the like. In some embodiments, there may be multiple frequency bands or ranges supported for a single protocol. The desire to support multiple communication protocols in an electronic device with limited space can provide a number of challenges with respect to antenna design. For example, when multiple protocols are required an antenna design in accordance with one embodiment needs to support bands covering ranges such as from about 746 MHz to about 787M Hz for cellular low band (LB) communications, from about 1.71 GHZ to about 2.155 GHz for cellular high band (HB) communications, from about 1.57 GHz to about 1.61 GHz for the GNSS band, and from about 2.4 GHz to about 2.48 GHz for the Bluetooth and/or Wi-Fi band. As mentioned, in a device such as a smart watch or biometric tracking device the space for placing antennas is very limited. Further, the coupling between antennas can be quite strong in such an electrically small device containing multiple antennas. As such, the antennas need to be carefully designed to achieve acceptable antenna performance. For some devices certain antenna designs are unable to coexist with other device components, such as an electrocardiogram (ECG) electrode interface for a biometric tracker. In the event that antenna designs are integrated in the device housing and/or exposed to external view, it can be desirable to design the antenna(s) in such a way as to achieve an attractive industrial design or aesthetic.

Accordingly, approaches in accordance with various embodiments provide antenna designs and assemblies that can support wireless communications over various frequency bands while accounting for at least some of the issues discussed herein with respect to such support. In various embodiments, the antenna concepts are integrated with housings with varying amounts of metal in the industrial design, such as full metal housings or metal housings with surface cuts. These antenna designs support different levels of antenna over-the-air (OTA) requirements as discussed herein.

Slot+Patch Antenna Design

Figure 2:
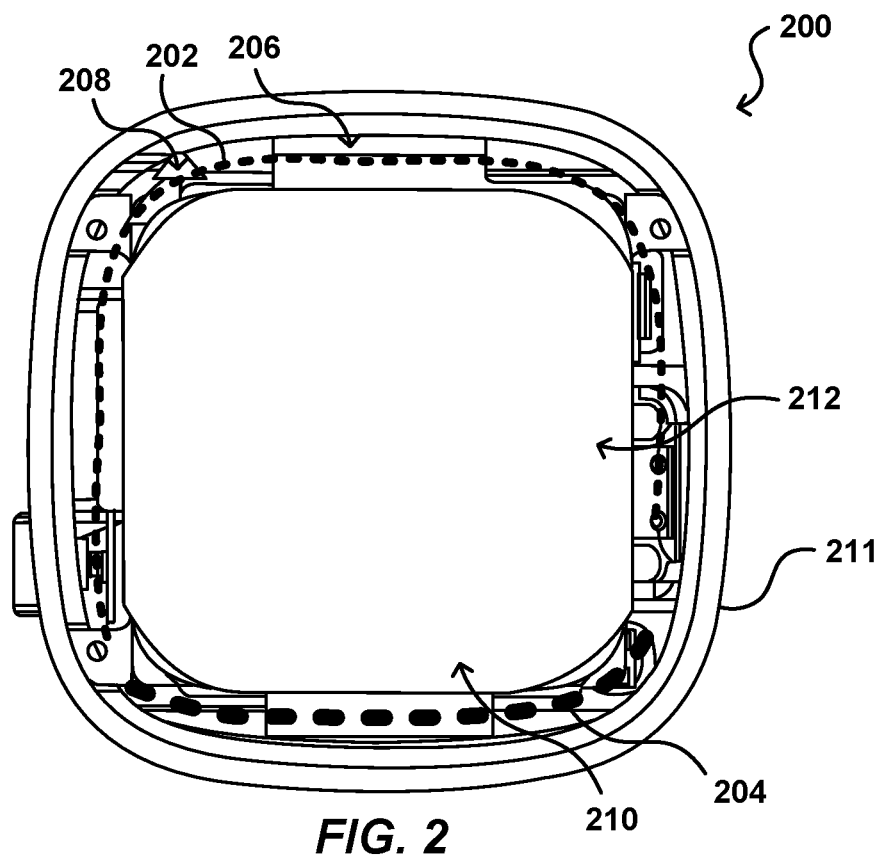
FIG. 2 illustrates a first top view of components of an example device including a slot and patch antenna assembly in accordance with various embodiments.

FIG. 2 illustrates a first top view 200 of components of an example device in accordance with one embodiment. This design incorporates a patch antenna design with a slot antenna. A patch antenna, or other microstrip antenna, can utilize a patch element as a relatively narrowband, widebeam antenna. A patch antenna can take the form of an element pattern etched in a metal trace bonded to a dielectric substrate such as a printed circuit board (PCB). As discussed later herein the PCB may include a PCB bracket that can help to insulate the PCB. The patch can include a metal layer bonded to the PCB to form a ground plane. While a rectangular shape is illustrated, various other shapes can be utilized for the patch element as well within the scope of the various embodiments. In some embodiments, wider bandwidth can be obtained by utilizing a conductive (e.g., metal) patch mounted above the ground plane using dielectric spacers.

Figure 3:
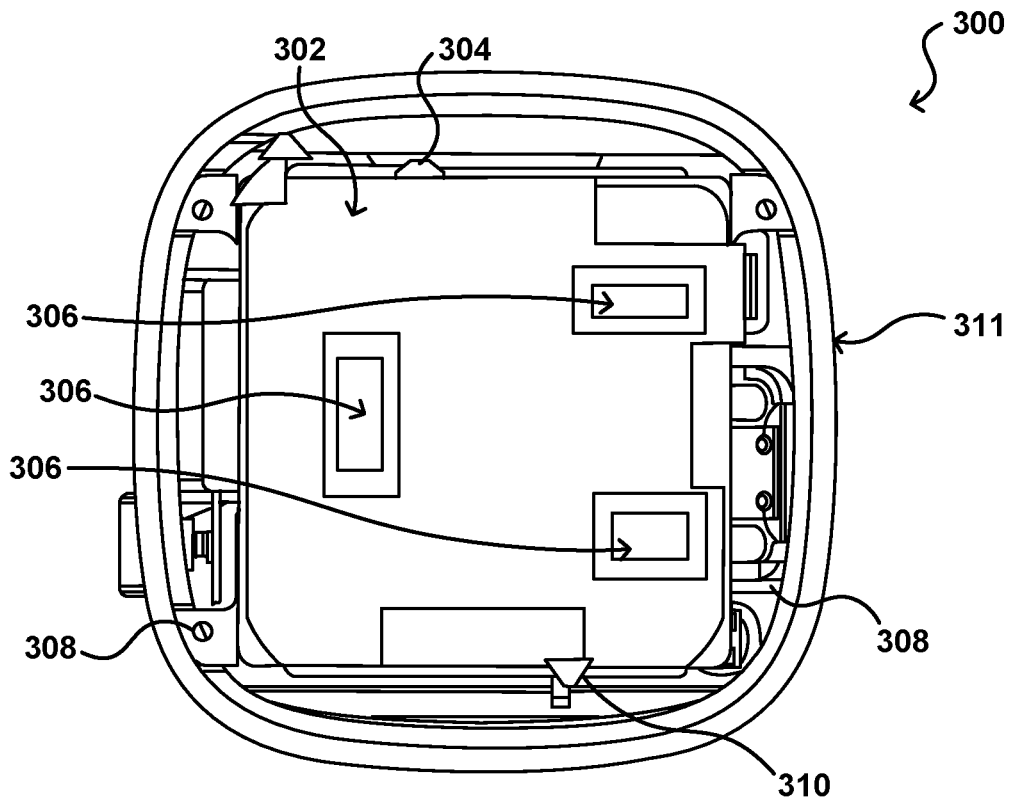
FIG. 3 illustrates a second top view of components of an example device including a slot and patch antenna assembly in accordance with various embodiments.

In FIG. 2, a pair of slot antennas 202, 204 are shown formed in a gap around the periphery of the device display 212 but inside the conductive device housing 214. Each of the slot antenna pair supports a different frequency range. The slots in this example are formed between the edges of the PCB and the interior of the metal housing. A first slot antenna 202 is separated from the second slot antenna 204 by a pair of slot grounds 308 illustrated in FIG. 3. The example device includes three different ports or antennas. A first port 206 can be used as a feed for the first slot antenna 202 for LTE and GPS communications, or only LTE communications in some embodiments. In FIG. 3, the patch antenna 302 component is illustrated, which can be a conductive plate and sits under the display 212 illustrated in FIG. 2. As illustrated in FIG. 2 and FIG. 3, a second port 208 can be used as a ground connection between the patch antenna 302 and the conductive housing 211. In some embodiments, a lumped component can be used to couple the patch antenna 302 to the conductive housing 211. A third port 210 can be used as a feed for the second slot antenna 204 for Wi-Fi and BLUETOOTH communications, and in some embodiments can be used for GPS communications as well, such as where the first port is only used for LTE communications. Various other protocols can utilize these ports as well in other embodiments. The addition of a passive patch antenna element provides a natural structure resonance for communications protocols such as the LTE low band protocol, using RF frequencies below 1.0 GHz. Such a design provides for relative ease of matching using an appropriate matching circuit. Such a design can also provide easier matching and the ability to utilize the high efficiency from the slot antenna 202. The patch can also generate another resonance separate from the slot antenna resonance(s) to cover additional bands, such as where the slot antenna has resonances covering the GNSS and LTE HB frequencies (~2 GHz) and the patch has a resonance covering the LTE LB frequencies (<1 GHz). The port 304 in FIG. 3 is a feed for the first slot antenna 202 coupled from the PCB to the battery bracket. In some of embodiments, the feed can be coupled from the PCB to the conductive housing. The port 310 is another feed for the second slot antenna 204 which can provide additional coverage for the BT/WiFi frequency range.

Figure 4:
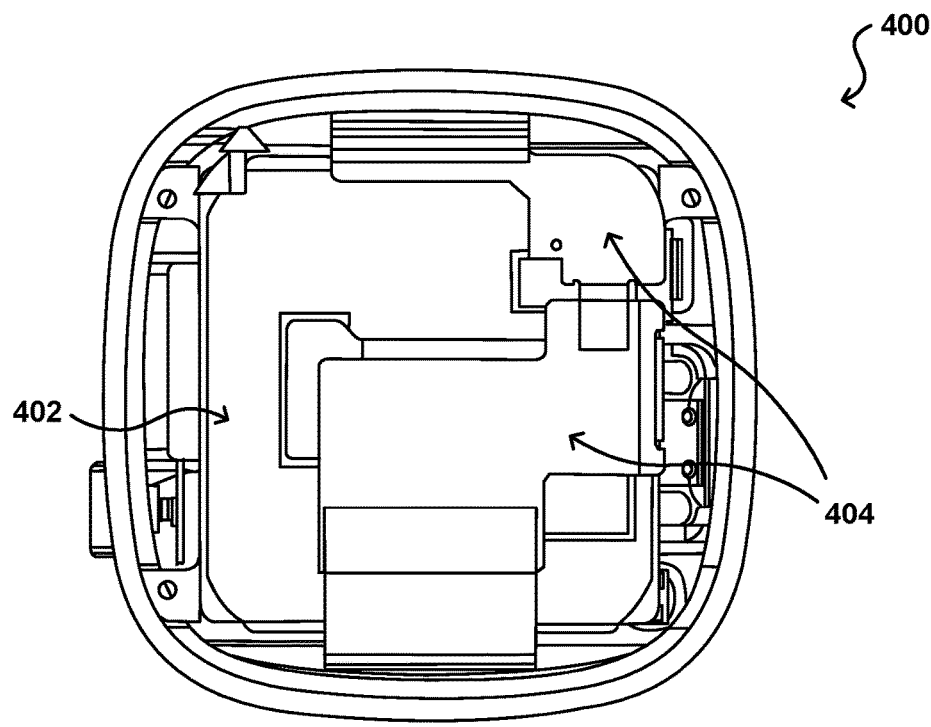
FIG. 4 illustrates a third top view of components of an example device including a slot and patch antenna assembly in accordance with various embodiments.

Various other components are available in the top view 300 of FIG. 3 as well. For example, the slot grounds 308 are two electric connections between the PCB 503 and the metal housing 311. They are the two grounding terminals shared for both slot antenna 202 and slot antenna 204. Meanwhile, they also provide the separations for the two slot antennas 202 and 204. The holes 306 are through holes cut out on the patch antenna plate to reduce the coupling from the patch antenna to tall components on the display flex or PCB. A feed 310 for the Wi-Fi and BLUETOOTH signals is illustrated, as well as an LTE and GNSS communications feed 304. The feed element can be a spring clip in various embodiments, creating a connection between the PCB and either the housing or battery bracket. In one embodiment, the slot antenna can be a single or multiple half-wavelength antenna that can be used for the LTE middle band (~2 GHz), GPS, and BT/WiFi bands. The patch antenna can be a parasitic conductive plate utilized to enable high efficiency LTE low band (<1 GHz) resonance excited by the slot antenna 202. This example device includes dual antenna cavities. FIG. 4 illustrates another top view 400 wherein display touch flexes 404 are illustrated over the NFC antenna 402.

Figure 5:
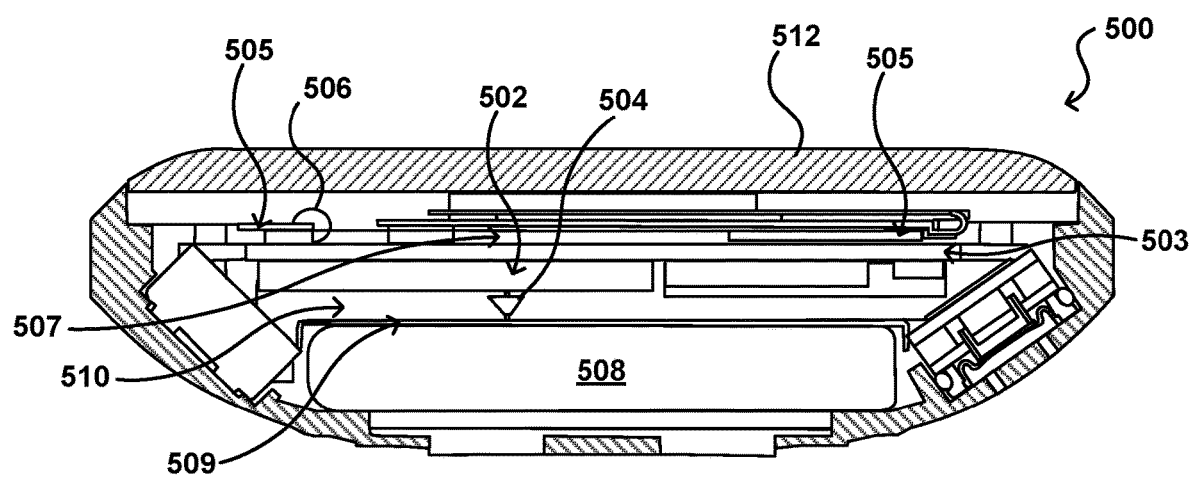
FIG. 5 illustrates a cross section view of components of an example device including a slot and patch antenna assembly in accordance with various embodiments.

FIG. 5 illustrates a cross-sectional view 500 showing an example stacking of components that can be utilized in accordance with various embodiments. In this example, the feed 504 for the first slot antenna is illustrated between the PCB 503 and the battery bracket 509. A patch cavity 507 is situated at a cut-away portion of the conductive patch 505. In this example, the battery bracket 509 is a conductive plate holding the battery 508 in place. The back cavity 510 is the gap between PCB 503 and battery bracket 509, or between PCB shield 502 and battery bracket 509. This back cavity 510 supports the antenna resonance mode for slot antenna 202 and slot antenna 204 (FIG. 2). The back cavity can be filled with components or shields mounted at the bottom side of PCB 503. In some embodiments, the back cavity 510 can be a gap loaded with dielectric materials.

Figure 6:
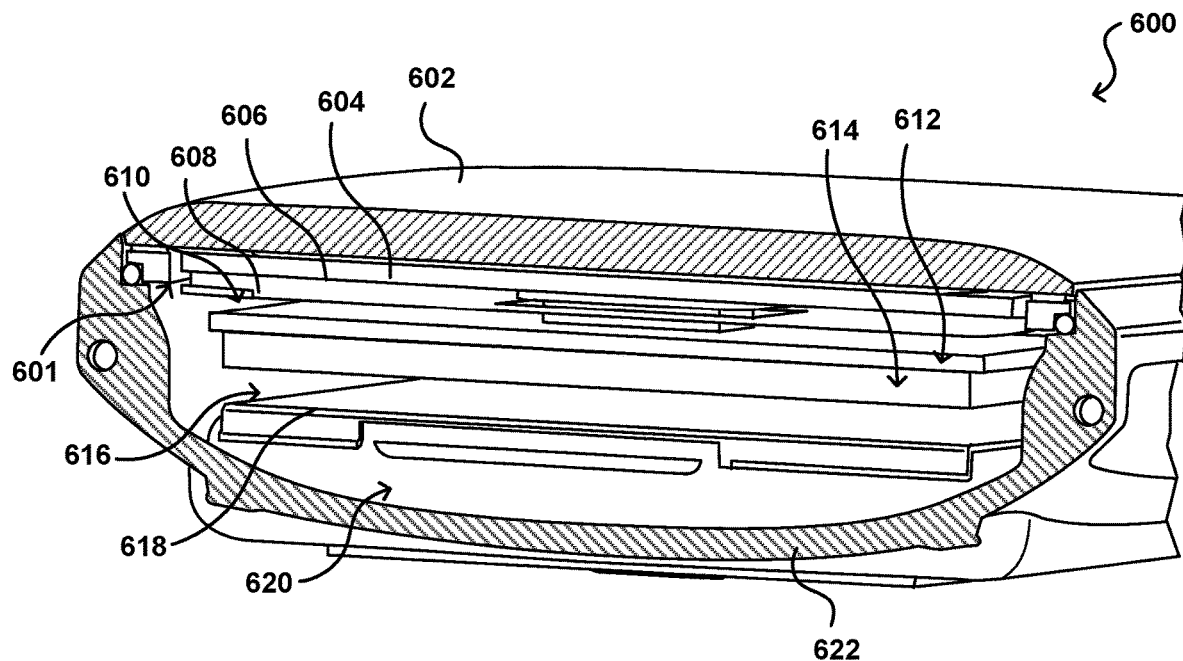
FIG. 6 illustrates a perspective, cross-section view of components of an example device including a slot and patch antenna assembly in accordance with various embodiments.

FIG. 6 illustrates another cross-sectional view 600 of an example device. In this example, the cover glass 602 overlies the display module 604. There is a gap 606 for the display and touch flexes and the NFC antenna between the display module 604 and the conductive patch 608. A patch antenna back cavity 610 is formed under the conductive patch 608 and above the printed circuit board (PCB) 612 which maintains the resonance mode for the patch antenna. The patch antenna 608 is coupled to the metal housing 622 through the port 601. The port 601 can be a metal spring contact directly coupled from the match patch 608 to the metal housing 622. In some embodiments, the port 601 can be a lumped component coupled from the conductive patch 608 to the metal housing 622 to adjust the resonance mode of the conductive patch 608. The PCB 612 and PCB shield 614 are positioned under the patch antenna back cavity, with the PCB shield formed to reduce electromagnetic interference (EMI) from the nearby components. A battery bracket 618 is used to hold the battery 620 in place within the housing, in this case with respect to the conductive metal housing 622. A slot antenna back cavity 616 is formed between the PCB shield 614 and the battery bracket 618.

Figure 7:
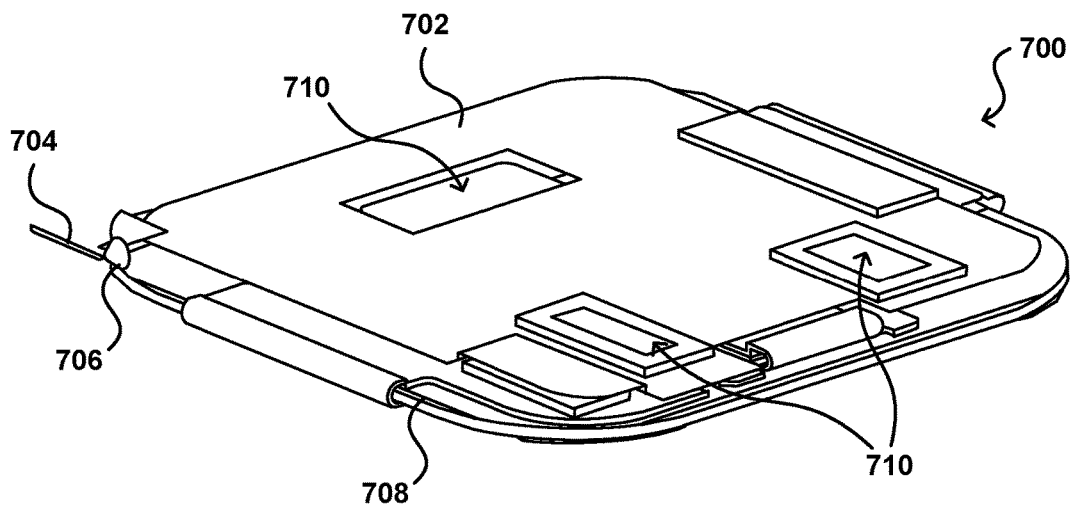
FIG. 7 illustrates an inverted perspective view of components of an example device including a slot and patch antenna assembly in accordance with various embodiments.

FIG. 7 illustrates a perspective view 700 with components of the stack flipped, such that the conductive patch 702 is illustrated on top of the touch-sensitive display module 708. In this view, a series lumped component 706 is illustrated that can be used to adjust the patch antenna resonance. A ground connection 704 to the conductive metal housing is also illustrated. A number of cutting holes 710 are illustrated in the patch antenna 702 that are used to reduce coupling from the components of the display module 708.

In some embodiments, the device can include an antenna matching circuit to achieve targeted antenna impedance. For example, an appropriate matching circuit can be used with the LTE, GNSS, and BLUETOOTH/Wi-Fi engines, providing high efficiency for all signals with acceptable return loss. Such an approach can improve both RF system transmission and reception. The antenna matching circuit design can be included on the PCB. The antenna matching circuit can be configured to connect the feed clip to an RF engine chipset on the PCB. The feed clip may also be provided by structures other than that shown, such as by a bonded wire, spring contact pin, a combination of such features or other features that provide for electrically-conductive contact between the monopole radiator and the printed circuit board. In some embodiments, the monopole radiator is routed in a clockwise pattern for efficient excitation of the slot antenna mode. In certain embodiments, the radiator performs better when placed closer to the display window.

In another embodiment, a slot only antenna may be used. Due to very low antenna impedance at LTE low band, the antenna matching circuit design can become very difficult to operate and sensitive from manufacturing tolerances. Thus, the matched antenna efficiency may be much lower than in a slot and patch antenna design due to the big insertion loss of the matching circuit for a pure slot antenna, with respect to that for a slot and patch antenna design. The two slot antennas and patch antenna will see three natural resonances for raw antenna impedance, and the matching circuits can be utilized to isolate the needed bands.

In some embodiments, a display window is mechanically coupled to the metal housing. The display window and the metal housing can form a sealed enclosure that is water resistant. The device includes a touch module and a display module, with the touch module configured to detect touch input on the display window. The display module is configured to display images or information through the display window. Below the touch and display modules, the metal plate is positioned within the metal housing to form the slot antenna (represented by the gaps between the metal housing or metal button bracket and the metal plate). The metal plate can be electrically coupled (e.g., grounded) to the metal housing through a grounding pin. It is to be understood that the number of grounding pins can vary depending on targeted performance characteristics. For example, the number of grounding pins can be at least 2, at least 3, at least 4, at least 5, and so forth.

An example device can include a component layer on a PCB. The component layer can include any appropriate components, as may include microprocessors, RAM (random access memory), ROM (read only memory), ASICs (application specific integrated circuit), FPGAs (field programmable gate array), surface mounted elements, integrated circuits, and the like. The PCB can provide electrical components and circuitry that directs and interprets electrical signals for the device. For example, the PCB can be electrically coupled to the display and touch modules to interpret touch input and to provide images or information to display. The PCB can include a ground plane portion. The PCB can also include a feed clip portion that does not include conductive elements other than where the antenna feed clip is mounted on and electrically coupled to the PCB. For example, the PCB can include a trace that electrically couples the ground plane area to the feed clip area, the feed clip being electrically coupled to the trace in the feed clip area. The ground plane may be provided by a large metalized area, conductive traces in a printed circuit board or flexible printed circuit board, a metal plate and/or surface within the metal housing, etc. The device can also include a vibrating motor to provide haptic feedback or to otherwise mechanically vibrate the device. The PCB can be grounded to the metal housing through one or more grounding screws that electrically couple the PCB to the metal housing. The battery can be about 0.05 mm below the metal plate. In some embodiments, a layer of a non-conductive, low RF loss, rigid material may be inserted to fit in the 0.05 mm gap to attach or otherwise mechanically couple the metal plate to the battery. In some embodiments, the battery is between about 0.01 mm and about 0.1 mm below the metal plate, between about 0.03 mm and about 0.7 mm below the metal plate, or between about 0.04 mm and about 0.06 mm below the metal plate. Between the battery and component layer, there is a dielectric gap (e.g. air or plastic or combination of air and plastic) which creates a back cavity for the slot antenna within an enclosed metal housing design. The dielectric gap may vary in height, but can be used to ensure isolation between the battery to any component on the component layer. The battery can be about 0.48 mm above the component layer. In some embodiments, the battery is between about 0.4 mm and about 0.6 mm above the component layer, between about 0.42 mm and about 0.55 mm above the component layer, or between about 0.45 mm and about 0.5 mm above component layer. In some embodiments, as described herein, a plastic bracket can be placed in this gap to support the battery above the component layer of the PCB.

Slot+IFA Antenna Design

Figure 8:
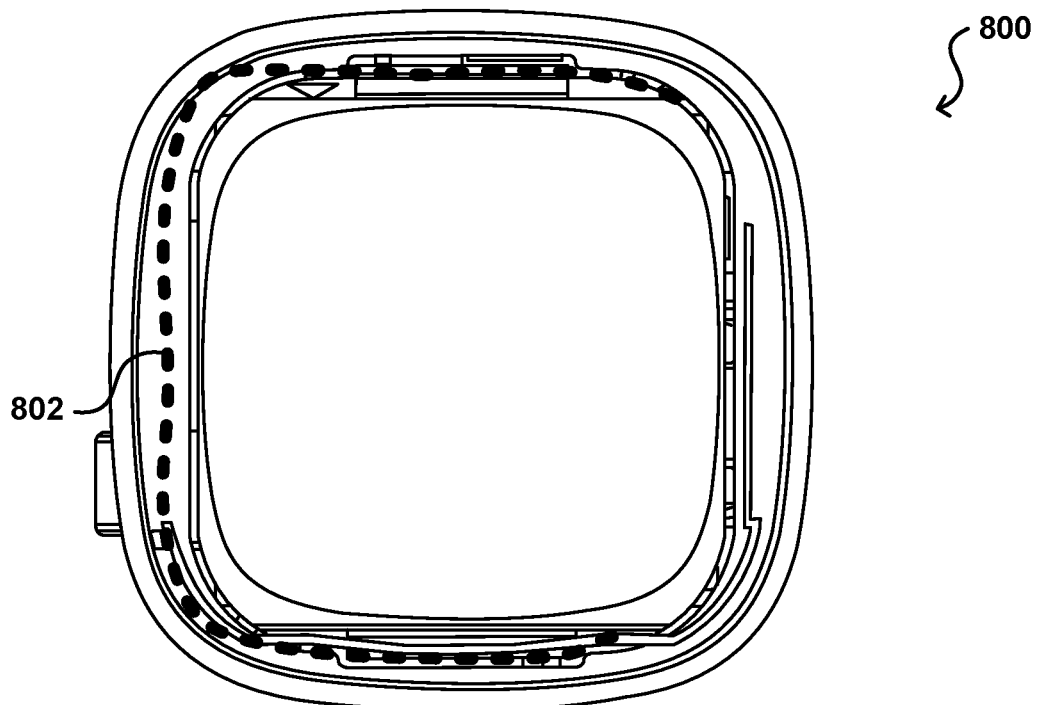
FIG. 8 illustrates a first top view of components of an example device including a slot and IFA antenna assembly in accordance with various embodiments.
Figure 9:
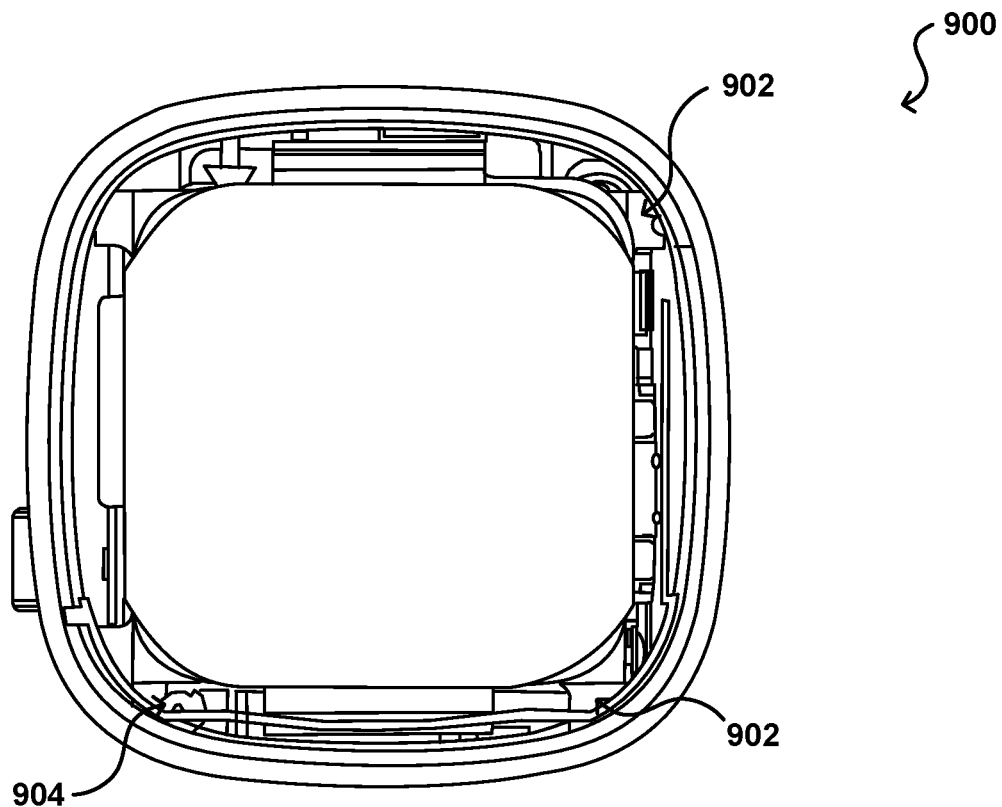
FIG. 9 illustrates a second top view of components of an example device including a slot and IFA antenna assembly in accordance with various embodiments.

FIG. 8 illustrates a top view 800 of an example device using a slot antenna and an inverted "F" antenna (IFA) design in accordance with one embodiment. In this example device, a single slot area 802 is created for the slot antenna. An IFA antenna design can attempt to utilize the same slot as the slot antenna for the IFA. The slot area can include multiple feed locations. The view 900 of FIG. 9 illustrates the slot grounds 902 designating the slot antenna area, as well as the location of an IFA antenna feed 904. An introduced IFA antenna element provides the natural resonance of the antenna at, for example, the LTE LB frequency range. The structure of the IFA grounding path, which is connected to the conductive device housing 1006 as illustrated in the cross-section view of FIG. 10, can be used as a contact point to excite the slot antenna. In conventional designs, the IFA ground would typically instead be on the PCB. The ability to use the grounding path in such a way can help to reduce the number of feed points for the antenna assembly. The use of the grounding path can also help to mitigate isolation issues by adding additional feeds to the device. The IFA-excited slot antenna can provide frequency coverage for other bands, such as for the GNSS and LTE HB (high-band) frequencies. A second feed can be used to directly feed the slot antenna, which can be used to generate the resonance to cover a frequency band at, for example, BLUETOOTH and/or Wi-Fi frequencies.

Figure 10:
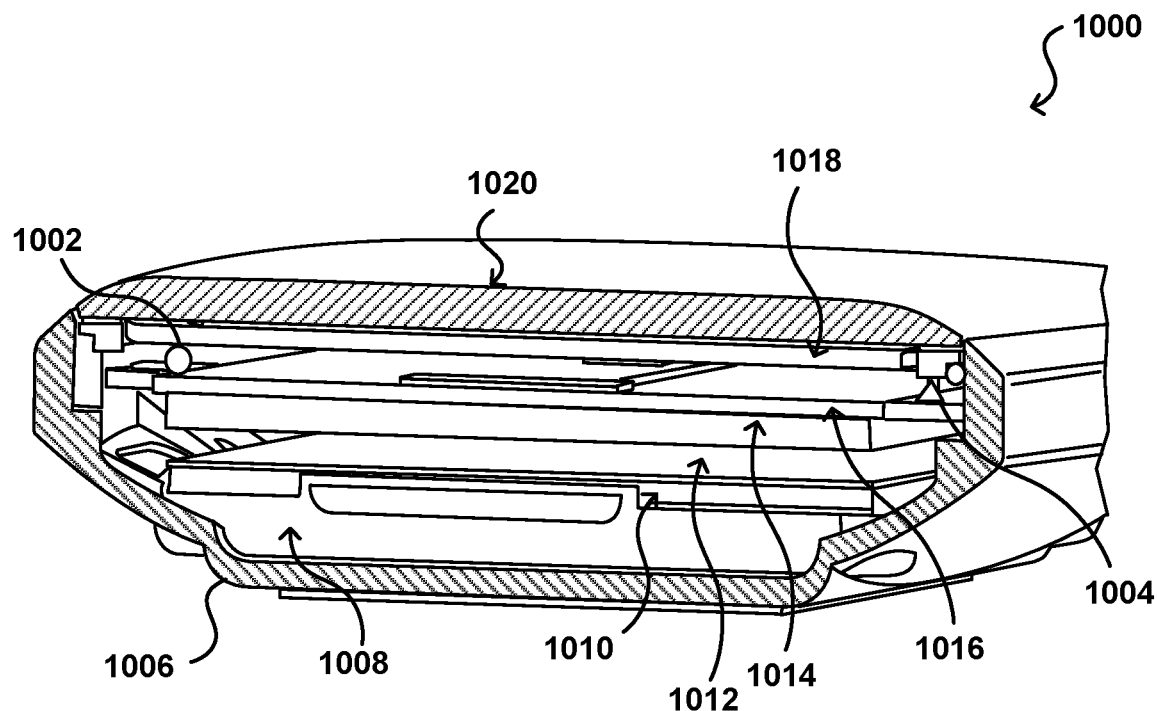
FIG. 10 illustrates a perspective, cross-section view of components of an example device including a slot and IFA antenna assembly in accordance with various embodiments.
Figure 11:
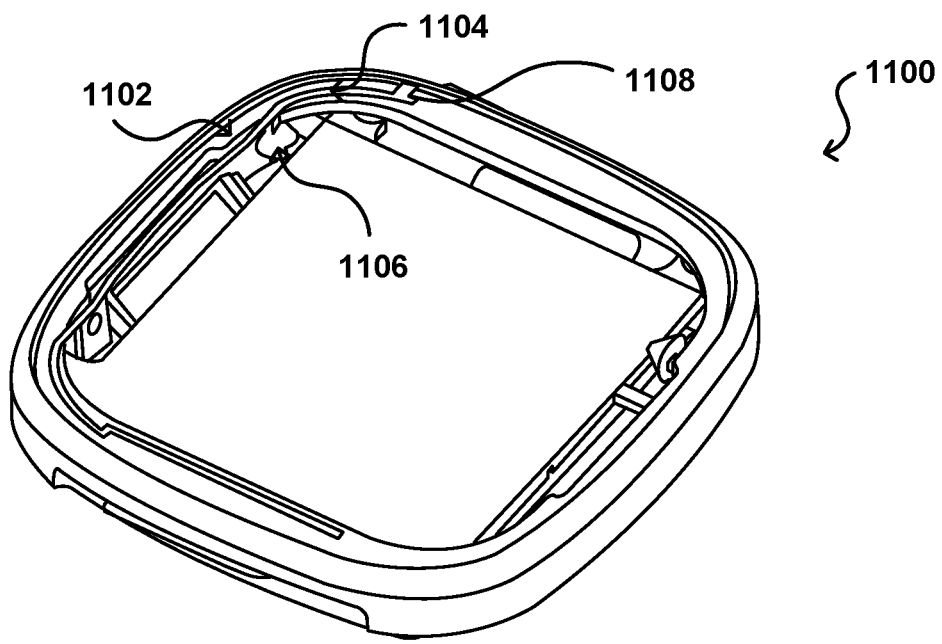
FIG. 11 illustrates an inverted cross-section view of components of an example device including a slot and IFA antenna assembly in accordance with various embodiments.

In the view 1000 of FIG. 10, a slot antenna feed 1002 is illustrated below the cover glass 1020 and display module 1018 of the electronic device to couple the PCB 1016 to the metal housing 1006. An IFA antenna feed 1004 is illustrated in the gap between the display module 1018 and the PCB 1016 to couple the IFA antenna to the PCB 1016, again shielded using an appropriate PCB shield 1014. The battery 1008 and battery bracket 1010 in this example are separated from the PCB 1016 by a back cavity 1012 as discussed herein. In one example device, the slot antenna can be utilized for single or multiple half wavelengths, such as may be useful for the LTE middle band (~2 GHz), GNSS, BLUETOOTH, and Wi-Fi frequency bands. The IFA antenna can be used at, for example, the LTE low band (<1 GHz) frequency range. The IFA grounding contact point can be used to excite the slot antenna mode as well, as discussed herein. In the perspective view 1100 of FIG. 11, which is inverted relative to the view 1000 of FIG. 10, the plastic sealing ledge 1102 and IFA antenna radiator 1104 are illustrated relative to the display and cover glass. The IFA feed point 1106 is illustrated, as well as the IFA grounding point 1108, which can be used to control operation of the IFA antenna. The IFA grounding point in this example also functions as an exciting point for the slot antenna.

Figure 12:
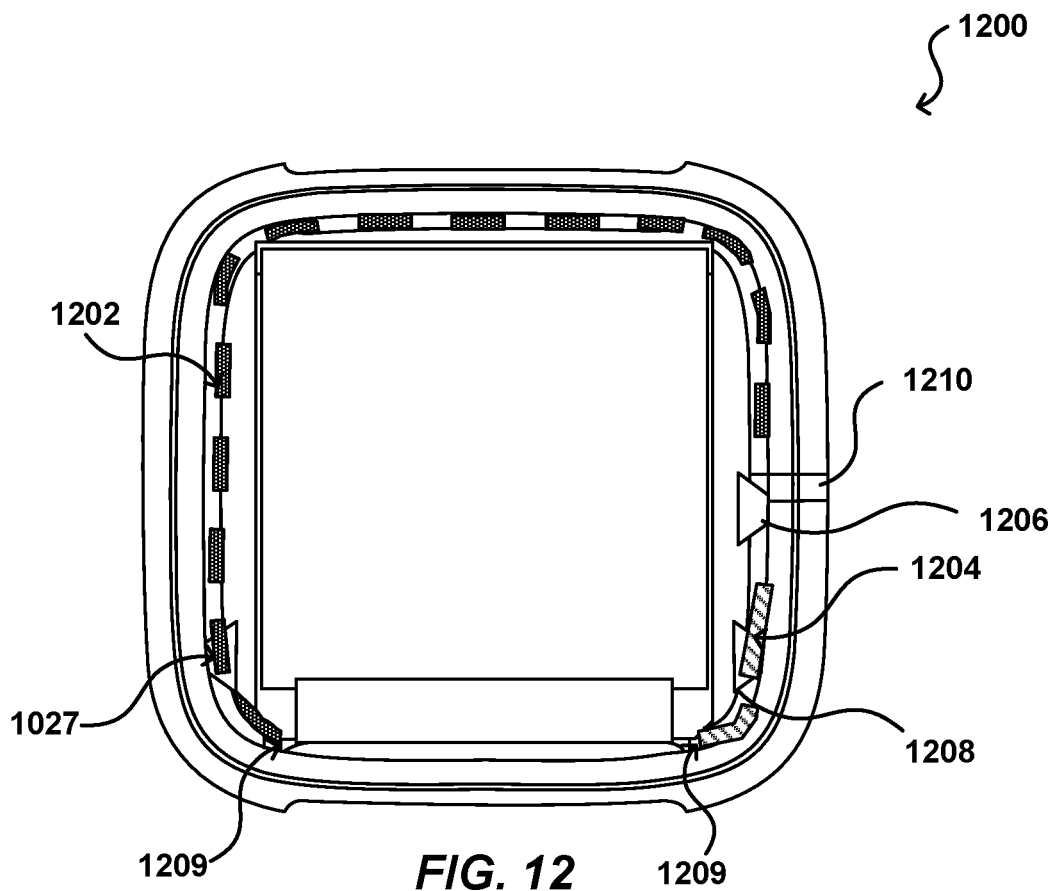
FIG. 12 illustrates a top view of components of an example device including a hybrid slot antenna assembly in accordance with various embodiments.

In another embodiment, a pure slot antenna or slot plus monopole antenna design can be utilized Similar to the slot and patch antenna, the IFA structure provides a higher antenna impedance compared to the pure slot or slot plus monopole antenna designs. The high antenna impedance helps to reduce the matching circuit loss and reduce the sensitivity antenna tolerances, compared to pure slot or slot plus monopole antenna designs at, for example, the LTE low band Hybrid Slot Antenna Design FIG. 12 illustrates a top view 1200 of components of an example device design incorporating what is referred to herein as a hybrid slot antenna. In this example, two hybrid slots are illustrated. The two hybrid slot design utilizes a combination design with two internal slot antenna portions 1202 and 1204 and a shared external slot antenna portion 1312 which is the plastic gap illustrated in FIG. 13. The internals slots 1202, 1204 are formed between the PCB 1308 and the conductive housing 1302 and utilize the cavity 1306 between the PCB 1308 and the battery 1304 or battery bracket [not shown]. The external slot 1312 is plastic gap in the conducting housing 1302 that extends from the opening for the display cover glass 1314 to the sensor window 1504 in FIG. 15. Feed points 1207, 1208 are illustrated respectively for hybrid slot 1202 and hybrid slot 1204. The two hybrid slot antennas are separated in part by a gap 1210 of plastic or another non-conductive material and two ground connections 1209 from PCB to the metal housing. The feed 1207 is coupled from PCB 1308 to conductive housing 1302 which supports resonances for LTE LB, HB, and GNSS or only for LTE LB and HB. The feed 1208 is coupled from PCB 1308 to conductive housing 1302 which supports resonances for Wi-Fi and BLUETOOTH or Wi-Fi, BLUETOOTH, and GNSS. Such an implementation can help significantly reduce the number of surface cuts needed, as well as the length of those surface cuts, compared to a conventional external slot antenna, which can significantly impact the flexibility in industrial design. A hybrid design can also achieve significantly better antenna efficiency compared to a purely internal slot antenna design, such has been used for full metal housing smart watches and fitness trackers, among other such devices.

Figure 13:
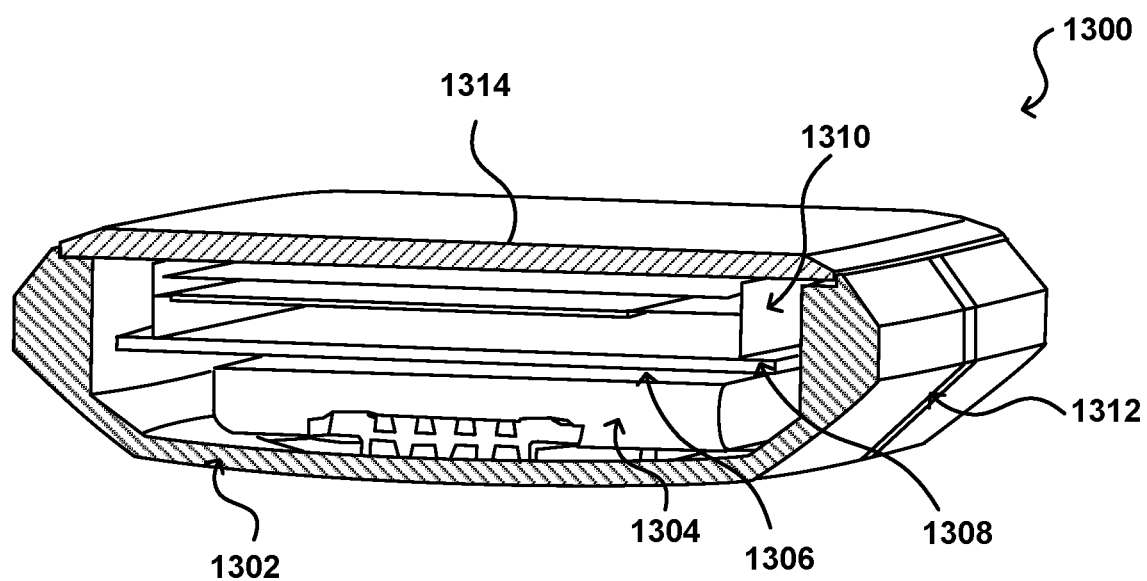
FIG. 13 illustrates a perspective, cross-section view of components of an example device including a hybrid slot antenna assembly in accordance with various embodiments.
Figure 14:
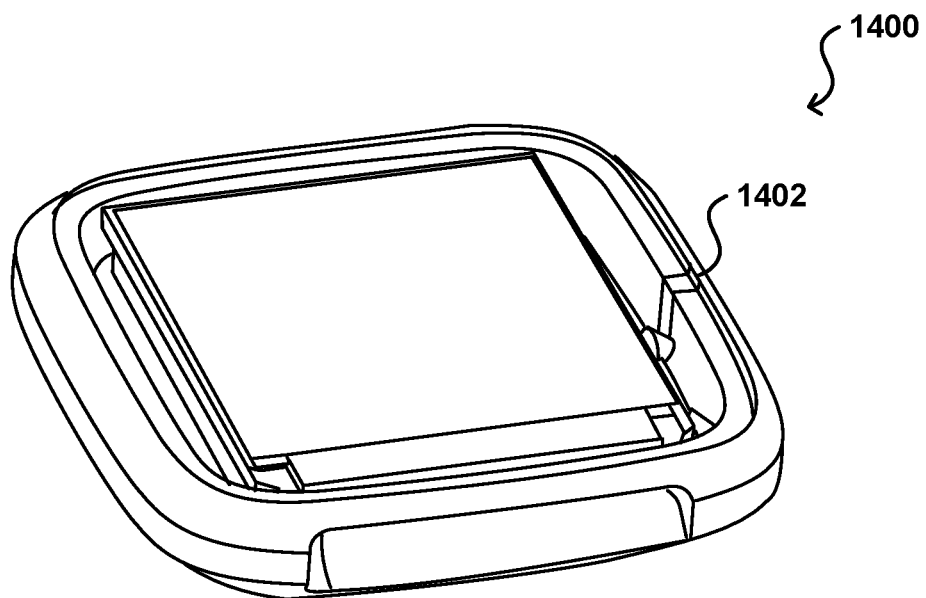
FIG. 14 illustrates an inverted perspective view of components of an example device including a hybrid slot antenna assembly in accordance with various embodiments.
Figure 15:
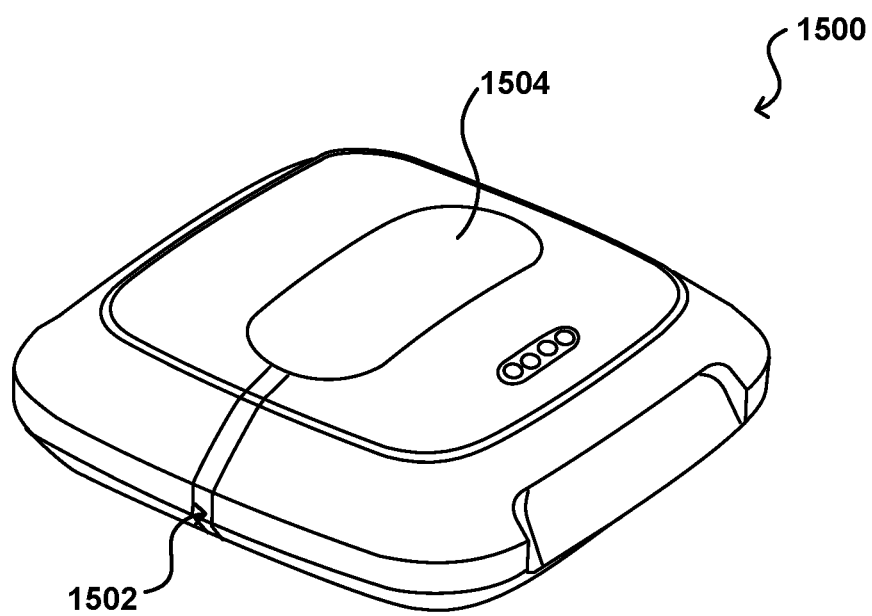
FIG. 15 illustrates an inverted perspective view of an example device including a hybrid slot antenna assembly in accordance with various embodiments.

FIG. 13 illustrates a cross-section view 1300 of the layered components of one such device. In this example, a display shield 1310 is illustrated with respect to the cover glass and display 1314. The battery 1304 is positioned inside the conductive housing 1302. The battery forms a back cavity 1306 in its separation from the PCB 1308. As illustrated, a plastic gap 1312 can be formed in the conductive housing 1302. In an example hybrid slot antenna device, each antenna portion can function as a quarter wavelength or higher order wavelength slot antenna. A quarter wavelength or higher order wavelength slot antenna can be used for the LTE low band (<1 GHz), LTE middle band (~2 GHz), GNSS, BLUETOOTH, and Wi-Fi band ranges, among others. For a hybrid slot antenna, each slot antenna has part of the antenna slot area inside the housing utilizing the gap between the PCB 1308 and the metal housing 1302. The display shield 1310 can isolate the display from the slot antennas 1202, 1204 and improve the performance of the slot antennas 1202, 1204. Further, part of the antenna slot is on the outer surface of housing utilizing the plastic gap 1312 in the housing, forming both an internal slot and an external slot. FIGS. 14 and 15 illustrate perspective views 1400, 1500, illustrating positions of the non-conductive gap with respect to other components of the example device a discussed herein.

In another embodiment, an internal slot antenna design can be used with a full metal housing. An external slot antenna design can also be used for a metal housing with surface cuts. Compared to an internal slot antenna design, a hybrid slot antenna can achieve much better antenna efficiency. Compared to the external slot antenna design, a hybrid slot antenna can help significantly reduce the number of metal surface cuts, as well as the length of each surface cut.

Figure 16:
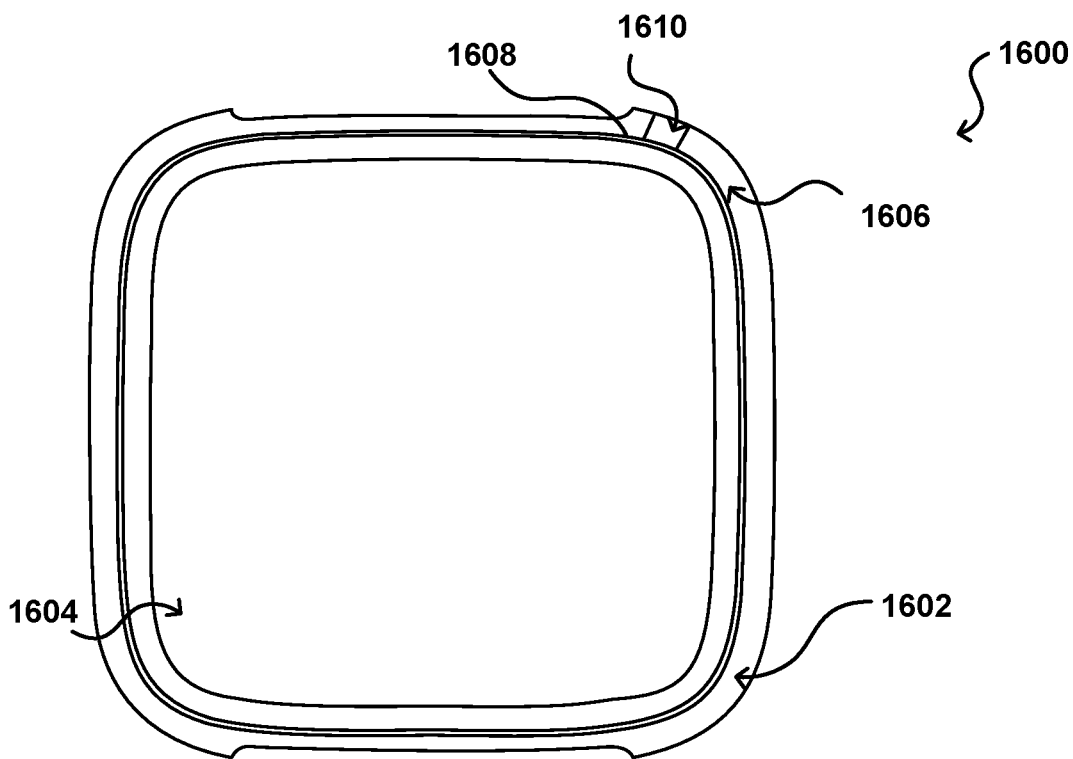
FIG. 16 illustrates a top view of components of an example device including an external slot antenna assembly in accordance with various embodiments.
Figure 17:
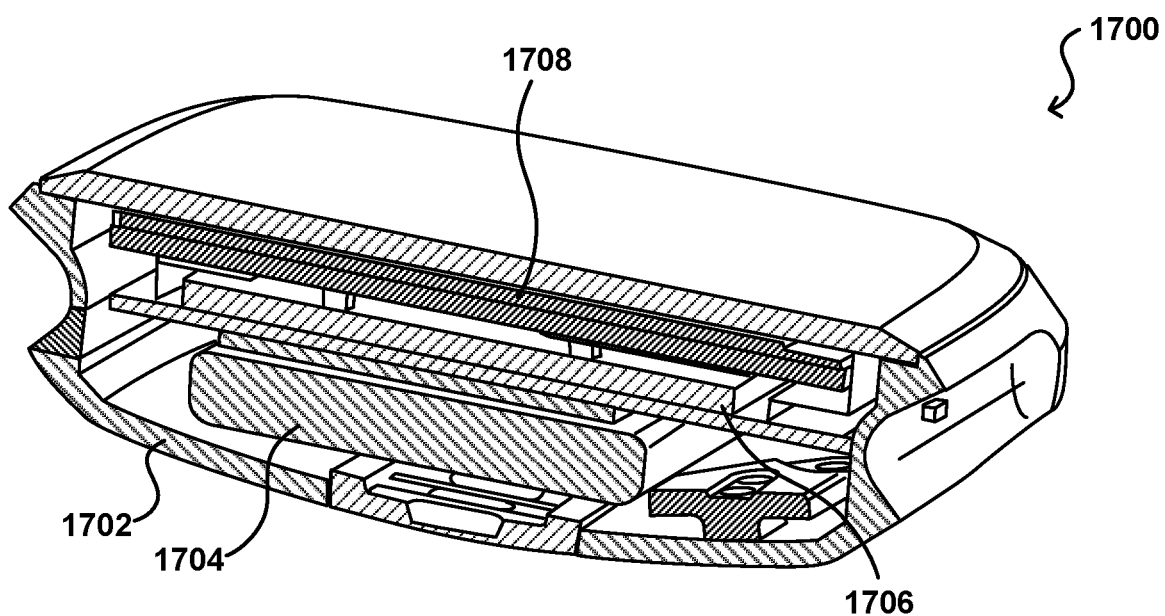
FIG. 17 illustrates a cross-section, perspective view of components of an example device including an external slot antenna assembly in accordance with various embodiments.
Figure 18:
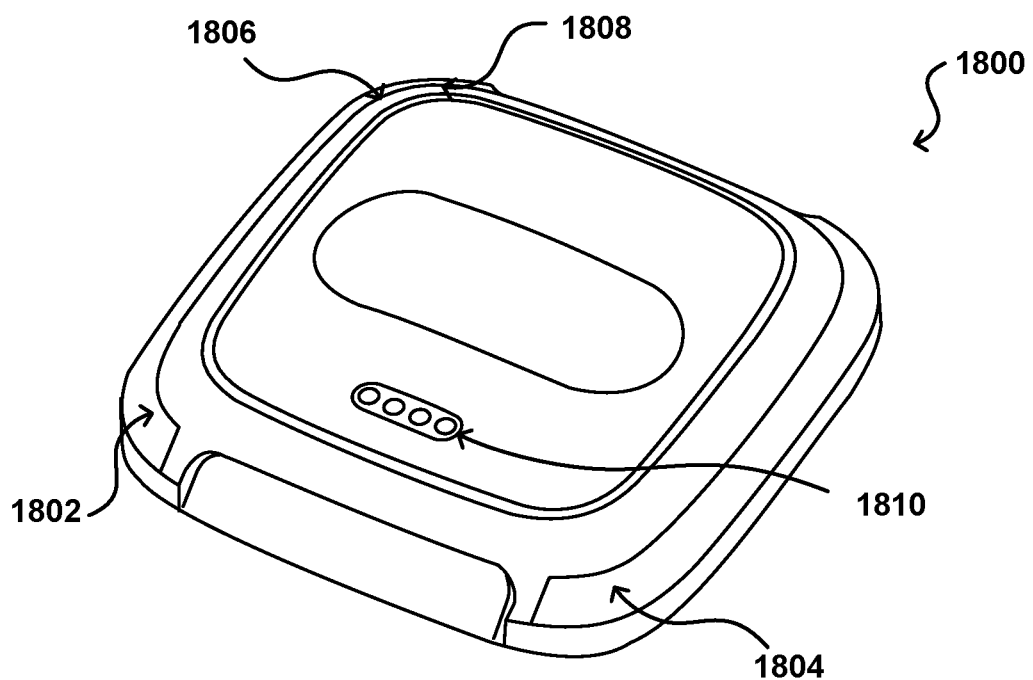
FIG. 18 illustrates a first perspective view of an example device including an external slot antenna assembly in accordance with various embodiments.
Figure 19:
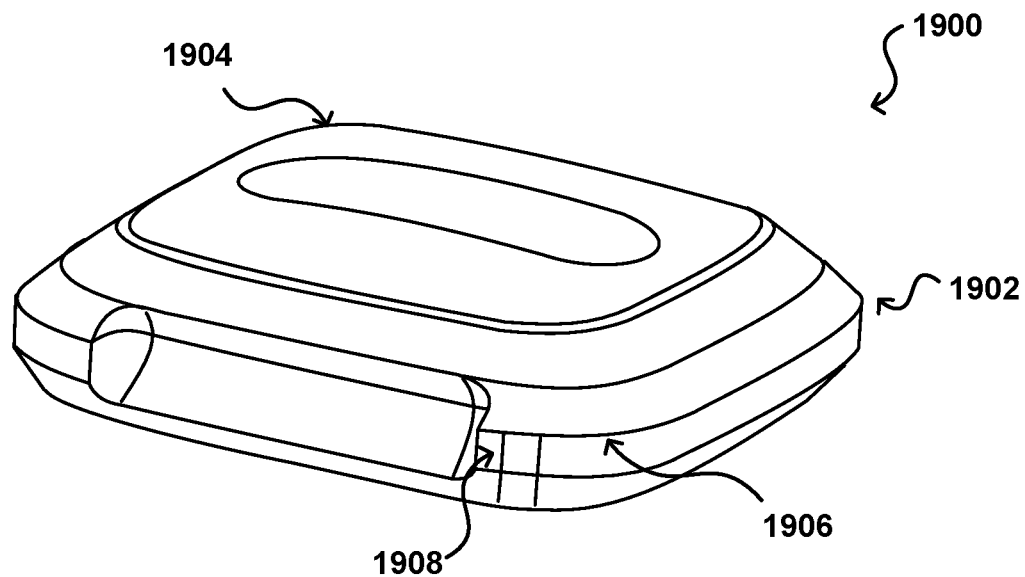
FIG. 19 illustrates a second perspective view of an example device including an external slot antenna assembly in accordance with various embodiments.

FIGS. 16-19 illustrate views 1600, 1700, 1800, 1900 of an external slot antenna implementation that can be utilized in accordance with various embodiments. In this example design, there are four ports 1602, 1604, 1606, 1608 illustrated, along with the non-conductive gap 1610 at an exterior of the housing as illustrated in FIG. 16. FIG. 17 illustrates a cross-section of the device, including components such as the display module 1708, PCB 1706, and battery 1704 inside the conductive housing 1702. FIGS. 18 and 19 illustrate back perspective views illustrating example placement of the ports 1802, 1804, 1806, 1808 and 1902, 1904, 1906, 1908. In this example, two of the ports 1602, 1604 are for antenna feeds and the other two ports 1606, 1608 can be lumped components, open connections, or short connections. In FIG. 18 a set of biometric components 1810 is displayed, as may include emitters and detectors capable of making biometric measurements for a person wearing the device as discussed herein. In some embodiments, ports 1902, 1904, 1906, and 1908 are aligned with ports 1802, 1804, 1806, 1808 and ports 1602, 1604, 1606, 1808.

Split Ring Antenna Design

Figure 20:
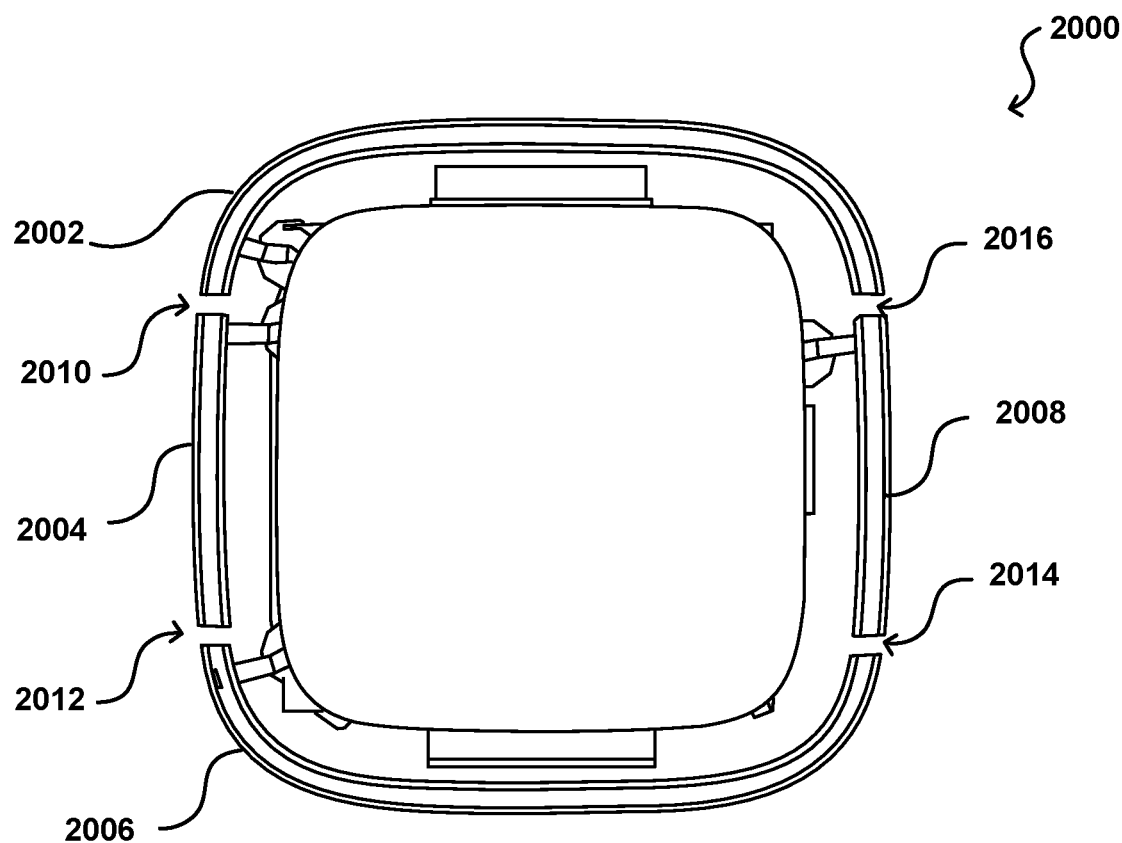
FIG. 20 illustrates a top view of components of an example device including a split ring antenna assembly in accordance with various embodiments.
Figure 21:
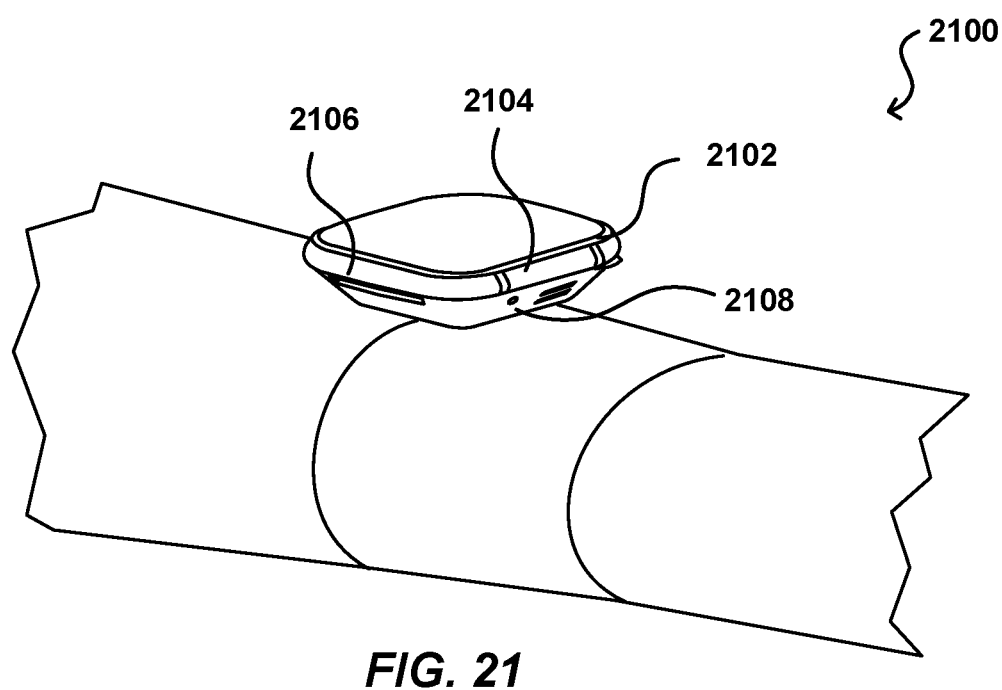
FIG. 21 illustrates a perspective view of an example device including a split ring antenna assembly in accordance with various embodiments.

FIG. 20 illustrates a top view 2000 of an example electronic device utilizing a split ring antenna design. A split ring antenna in accordance with one embodiment features separate antenna elements 2002, 2004, 2006, 2008 separated by splits 2010, 2012, 2014, 2016 introduced on a ring-like conductive element. A first antenna portion 2008 can be used for BLUETOOTH and Wi-Fi communications, a second antenna portion 2002 for LTE low band communications, a third antenna portion 2006 for GPS communications, and a fourth antenna portion 2004 for LTE high band communications, although other communications and element portions can be utilized as well within the scope of the various embodiments. In this example the multi-part element is situated on or near the top side of the housing 2108 as illustrated in the exterior perspective view 2100 of FIG. 21. Three of the parts 2102, 2104, 2106 are illustrated in FIG. 21, which correspond to three of the four antenna portions. A process such as nano-molding can be used to obtain the gaps in a plastic housing, creating four monopole antennas from the split metal ring. A split ring antenna design allows the designer to regulate the directivity of the GPS radiation pattern towards the sky, effectively increasing UHIS (Upper Hemisphere) and PIGS (Partial Isotropic GPS Sensitivity) efficiencies for common use cases, such as a user wearing the device while running. Such a design can have a higher antenna efficiency than for antenna designs integrated in a full metal housing, particularly for low band frequencies such as LTE Band 13. The low band is currently a preferred frequency band of at least some cellular operators due to the propagation benefits of the lower frequency. This benefit enables the design to meet the cellular operator specifications for Voice over LTE, for example, where a minimum total radiated power is required to accept the device in their network. A split antenna design also enables the re-use of the antenna elements as ECG electrodes. For example, the two larger elements can be used as one ECG electrode, which may interface with the user, as well as a bottom of the device functioning as the other electrode. Such a design enables the use of bandpass filters and other such elements to isolate the individual antenna elements.

In one example embodiment, the device housing can be mostly plastic or polymer, while the four antenna elements are implemented using a split metal ring, or other such conductive element. An antenna matching circuit and one or more filters can be used to manage the isolation between each of the antenna elements of the split ring. In an alternative embodiment, a plastic housing can be used with an external ECG electrode and at least one internal monopole antenna. FIGS. 22 and 23 illustrate example circuits that can be used for different portion options. For example, the circuit 2200 of FIG. 22 can be used for a four engine ports option, including RF ports for BLUETOOTH/Wi-Fi, GPS, LTE low band, and LTE high band. Appropriate bandpass filters can be applied to all but the LTE low band port, and appropriate antenna matching circuitry used for each respective port. The circuit 2300 of FIG. 23 can be used for a three engine port option, including RF ports for BLUETOOTH/Wi-Fi, GNSS, and LTE high band/low band. An LTE diplexer can be used for the LTE port to split the low band and high band, with a GPS extractor potentially used as a GPS band notch filter. A bandpass filter can be applied to the BLUETOOTH/Wi-Fi port, and appropriate antenna matching circuitry used for each respective port.

Dielectrically Loaded PIFA Design

Figure 24:
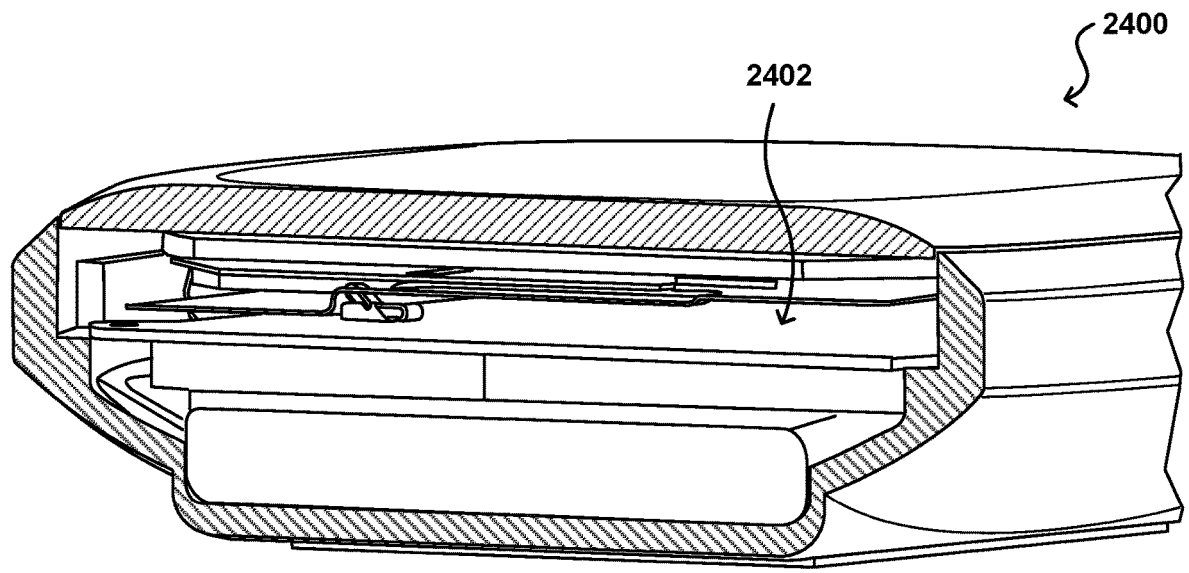
FIG. 24 illustrates a cross-section, perspective view of components of an example device including a dielectrically loaded PIFA assembly in accordance with various embodiments.
Figure 25:
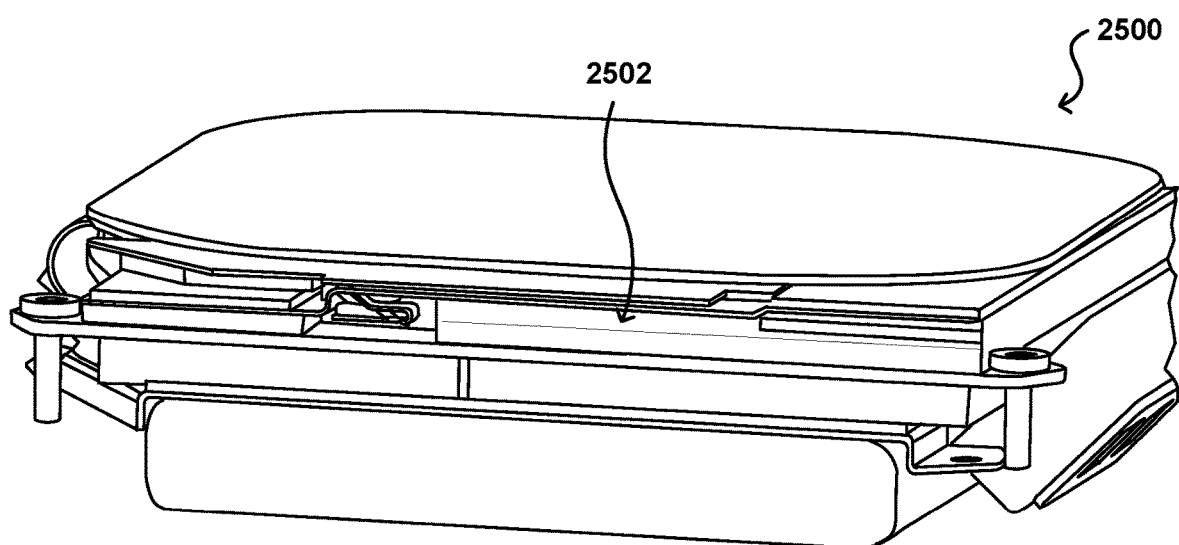
FIG. 25 illustrates a perspective view of components of an example device including a dielectrically loaded PIFA assembly in accordance with various embodiments.

FIG. 24 illustrates a cross-section view 2400 showing components of an example device utilizing a dielectrically loaded planar inverted "F" antenna (PIFA) in accordance with one embodiment. In this example, the device takes advantage of a conductive display bracket and an inverted PCB. The dielectrically loaded PIFA in this example is integrated inside a full metal housing consisting of a conductive display bracket, where the conductive display bracket and the PCB forms the planar IFA antenna. The conductive display bracket houses the display flexes and display assembly, with an NFC antenna on top. An inverted PCB is positioned below the bracket to form a cavity 2402, also illustrated 2502 in the perspective view 2500 of FIG. 25. The cavity is loaded with a dielectric material to shift the natural resonance of the structure to the LTE low band that is to be covered. In one embodiment, the design can cover the LTE low band as well as a range for BLUETOOTH and Wi-Fi. A remainder of the frequency bands, such as for GPS and LTE Band 4, can be provided using monopole antennas integrated in the sides of the display. An advantage of such a design is that the natural resonance of the structure provides for good impedance at the low band, enabling the designer to match it to the recommended −6 dB return loss that may be required by the transceiver to operate properly. Such an approach can help reduce the matching losses and result in much higher efficiency than other designs featuring conventional monopole antennas. In an alternative embodiment, one or more monopole antennas can be used inside a metal housing. Such a design can have very low impedance, however, and can result in very high matching losses which may result in lower total antenna efficiency.

As mentioned, the various embodiments can be implemented as a system that includes one or more tracking devices for a given user. In some instances aspects of the embodiments may be provided as a service, which users can utilize for their devices. Other tracker providers may also subscribe or utilize such a service for their customers. In some embodiments an application programming interface (API) or other such interface may be exposed that enables collected body data, and other information, to be received to the service, which can process the information and send the results back down to the tracker, or related computing device, for access by the user. In some embodiments at least some of the processing may be done on the tracking or computing device itself, but processing by a remote system or service may allow for more robust processing, particularly for tracking devices with limited capacity or processing capability.

FIG. 26 illustrates components of an example tracker system 2600 that can be utilized in accordance with various embodiments. In this example, the device includes at least one processor 2602, such as a central processing unit (CPU) or graphics processing unit (GPU) for executing instructions that can be stored in a memory device 2604, such as may include flash memory or DRAM, among other such options. As would be apparent to one of ordinary skill in the art, the device can include many types of memory, data storage, or computer-readable media, such as data storage for program instructions for execution by a processor. The same or separate storage can be used for images or data, a removable memory can be available for sharing information with other devices, and any number of communication approaches can be available for sharing with other devices. The device typically will include some type of display 2606, such as a touch screen, organic light emitting diode (OLED), or liquid crystal display (LCD), although devices might convey information via other means, such as through audio speakers or projectors.

A tracker or similar device will include at least one motion detection sensor, which as illustrated can include at least one I/O element 2610 of the device. Such a sensor can determine and/or detect orientation and/or movement of the device. Such an element can include, for example, an accelerometer, inertial sensor, altimeter, or gyroscope operable to detect movement (e.g., rotational movement, angular displacement, tilt, position, orientation, motion along a non-linear path, etc.) of the device. An orientation determining element can also include an electronic or digital compass, which can indicate a direction (e.g., north or south) in which the device is determined to be pointing (e.g., with respect to a primary axis or other such aspect). A device may also include an I/O element 2610 for determining a location of the device (or the user of the device). Such a positioning element can include or comprise a GPS or similar location-determining element(s) operable to determine relative coordinates for a position of the device. Positioning elements may include wireless access points, base stations, etc., that may either broadcast location information or enable triangulation of signals to determine the location of the device. Other positioning elements may include QR codes, barcodes, RFID tags, NFC tags, etc., that enable the device to detect and receive location information or identifiers that enable the device to obtain the location information (e.g., by mapping the identifiers to a corresponding location). Various embodiments can include one or more such elements in any appropriate combination. The I/O elements may also include one or more biometric sensors, optical sensors, barometric sensors (e.g., altimeter, etc.), and the like.

As mentioned above, some embodiments use the element(s) to track the location and/or motion of a user. Upon determining an initial position of a device (e.g., using GPS), the device of some embodiments may keep track of the location of the device by using the element(s), or in some instances, by using the orientation determining element(s) as mentioned above, or a combination thereof. As should be understood, the algorithms or mechanisms used for determining a position and/or orientation can depend at least in part upon the selection of elements available to the device. The example device also includes one or more wireless components 2612 operable to communicate with one or more electronic devices within a communication range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections as known in the art. The device also includes one or more power components 2608, such as may include a battery operable to be recharged through conventional plug-in approaches, or through other approaches such as capacitive charging through proximity with a power mat or other such device. In some embodiments the device can include at least one additional input/output device 2610 able to receive conventional input from a user. This conventional input can include, for example, a push button, touch pad, touch screen, wheel, joystick, keyboard, mouse, keypad, or any other such device or element whereby a user can input a command to the device. These I/O devices could even be connected by a wireless infrared or Bluetooth or other link as well in some embodiments. Some devices also can include a microphone or other audio capture element that accepts voice or other audio commands. For example, a device might not include any buttons at all, but might be controlled only through a combination of visual and audio commands, such that a user can control the device without having to be in contact with the device.

As mentioned, many embodiments will include at least some combination of one or more emitters 2616 and one or more detectors 2618 for measuring data for one or more metrics of a human body, such as for a person wearing the tracker device. In some embodiments this may involve at least one imaging element, such as one or more cameras that are able to capture images of the surrounding environment and that are able to image a user, people, or objects in the vicinity of the device. The image capture element can include any appropriate technology, such as a CCD image capture element having a sufficient resolution, focal range, and viewable area to capture an image of the user when the user is operating the device. Methods for capturing images using a camera element with a computing device are well known in the art and will not be discussed herein in detail. It should be understood that image capture can be performed using a single image, multiple images, periodic imaging, continuous image capturing, image streaming, etc. Further, a device can include the ability to start and/or stop image capture, such as when receiving a command from a user, application, or other device. The example device includes emitters 2616 and detectors 2618 capable of being used for obtaining other biometric data, which can be used with example circuitry discussed herein.

If included, a display 2606 may provide an interface for displaying data, such as HR, ECG data, blood oxygen saturation ($SpO_2$) levels, and other metrics of the user. In an embodiment, the device includes a wristband and the display is configured such that the display faces away from the outside of a user's wrist when the user wears the device. In other embodiments, the display may be omitted and data detected by the device may be transmitted using the wireless networking interface via near-field communication (NFC), Bluetooth, Wi-Fi, or other suitable wireless communication protocols over at least one network 2620 to a host computer 2622 for analysis, display, reporting, or other such use.

The memory 2604 may comprise RAM, ROM, FLASH memory, or other non-transitory digital data storage, and may include a control program comprising sequences of instructions which, when loaded from the memory and executed using the processor 2602, cause the processor 2602 to perform the functions that are described herein. The emitters 2616 and detectors 2618 may be coupled to a bus directly or indirectly using driver circuitry by which the processor 2602 may drive the light emitters 2616 and obtain signals from the light detectors 2618. The host computer 2622 communicate with the wireless networking components 2612 via one or more networks 2620, which may include one or more local area networks, wide area networks, and/or internetworks using any of terrestrial or satellite links. In some embodiments, the host computer 2622 executes control programs and/or application programs that are configured to perform some of the functions described herein.

In various embodiments, approaches discussed herein may be performed by one or more of: firmware operating on a monitoring or tracker device or a secondary device, such as a mobile device paired to the monitoring device, a server, host computer, and the like. For example, the monitoring device may execute operations relating to generating signals that are uploaded or otherwise communicated to a server that performs operations for removing the motion components and creating a final estimate value for physiological metrics. Alternatively, the monitoring device may execute operations relating to generating the monitoring signals and removing the motion components to produce a final estimate value for physiological metrics local to the monitoring device. In this case, the final estimate may be uploaded or otherwise communicated to a server such as host computer that performs other operations using the value.

An example monitoring or tracker device can collect one or more types of physiological and/or environmental data from one or more sensor(s) and/or external devices and communicate or relay such information to other devices (e.g., host computer or another server), thus permitting the collected data to be viewed, for example, using a web browser or network-based application. For example, while being worn by the user, a tracker device may perform biometric monitoring via calculating and storing the user's step count using one or more sensor(s). The tracker device may transmit data representative of the user's step count to an account on a web service (e.g., www.fitbit.com), computer, mobile phone, and/or health station where the data may be stored, processed, and/or visualized by the user. The tracker device may measure or calculate other physiological metric(s) in addition to, or in place of, the user's step count. Such physiological metric(s) may include, but are not limited to: energy expenditure, e.g., calorie burn; floors climbed and/or descended; HR; heartbeat waveform; HR variability; HR recovery; respiration, $SpO_2$, blood volume, blood glucose, skin moisture and skin pigmentation level, location and/or heading (e.g., via a GPS, global navigation satellite system (GLONASS), or a similar system); elevation; ambulatory speed and/or distance traveled; swimming lap count; swimming stroke type and count detected; bicycle distance and/or speed; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

An example tracker or monitoring device may also measure or calculate metrics related to the environment around the user (e.g., with one or more environmental sensor(s)), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, a tracker device (and/or the host computer and/or another server) may collect data from one or more sensors of the device, and may calculate metrics derived from such data. For example, a tracker device may calculate the user's stress or relaxation levels based on a combination of HR variability, skin conduction, noise pollution, and/or sleep quality. In another example, a tracker device may determine the efficacy of a medical intervention, for example, medication, based on a combination of data relating to medication intake, sleep, and/or activity. In yet another example, a tracker device may determine the efficacy of an allergy medication based on a combination of data relating to pollen levels, medication intake, sleep and/or activity. These examples are provided for illustration only and are not intended to be limiting or exhaustive.

An example monitoring device may include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. A monitoring system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. An electronic device, comprising:
a conductive housing;
a display module positioned at an opening of the conductive housing;
a cover overlying the display module;
a power source contained within the conductive housing;
a printed circuit board (PCB) having one or more edges, respective portions of a gap between the one or more edges and an interior surface of the conductive housing forming a pair of slot antennas;
a conductive patch antenna formed in a cavity between the PCB and the display module, the conductive patch antenna spaced apart from the display module such that a gap is defined between the display module and the conductive patch antenna; and
antenna matching circuitry coupling one or both of the slot antennas to the conductive patch antenna, wherein electromagnetic fields induce the pair of slot antennas and the conductive patch antenna to transmit or receive radio frequency (RF) signals over respective frequency bands.

2. The electronic device of claim 1, wherein one of the slot antennas is configured to transmit or receive RF signals over respective frequency band(s) between 1 GHz and 3 GHz, and wherein the other slot antenna coupled with the conductive patch antenna is configured to transmit or receive RF signals over respective frequency band(s) less than about 2 GHz.

3. The electronic device of claim 1, wherein the slot antennas are each configured to transmit or receive communications for at least one of BLUETOOTH, Wi-Fi, global positioning system (GPS), or Long-Term Evolution (LTE) communications.

4. The electronic device of claim 1, wherein the conductive patch antenna is a parasitic patch antenna excited by one slot antenna and configured to transmit or receive LTE low band communications.

5. The electronic device of claim 1, wherein the PCB and a conductive bracket form a back cavity comprising a dielectric gap and facilitating resonance of the slot antennas.

6. The electronic device of claim 1, wherein the natural resonance of the antenna is at the LTE low-band frequency range.

7. The electronic device of claim 1, wherein at least one slot antenna of the pair of slot antennas is a half-wavelength slot antenna.

8. The electronic device of claim 1, further comprising at least two slot grounding pins for tuning the resonances of the pair of slot antennas.

9. The electronic device of claim 1, further comprising a respective feed element for each of the pair of slot antennas.

10. The electronic device of claim 1, wherein the PCB further includes at least one of a microprocessors, memory, application specific integrated circuit (ASIC), or field programmable gate array (FPGA).

11. An electronic device, comprising:
a conductive housing
a display module positioned at an opening of the conductive housing;
a cover overlying the display module;
a slot antenna formed in a gap between a printed circuit board (PCB) and an interior surface of the conductive housing;
a conductive patch antenna formed in a cavity between the PCB and the display module, the conductive patch antenna spaced apart from the display module such that a gap is defined between the display module and the conductive patch antenna; and
antenna matching circuitry coupling the slot antenna and the conductive patch antenna, wherein electromagnetic fields induce the slot antenna and the conductive patch antenna to transmit or receive radio frequency (RF) signals over respective frequency bands.

12. The electronic device of claim 11, wherein the slot antenna coupled to the conductive patch antenna is configured to transmit or receive RF signals over two respective frequency bands below about 3 GHz.

13. The electronic device of claim 11, wherein the conductive patch antenna is a parasitic patch antenna excited by the slot antenna and configured to transmit or receive LTE low band communications.

14. The electronic device of claim 11, wherein the PCB and a conductive bracket form a back cavity comprising a dielectric gap and facilitating resonance of the slot antennas.

15. A wearable computing device, comprising:
a device housing;
a strap connected to the device housing and enabling the wearable computing device to be worn by a user;
a processor;
a display module for displaying content under instruction of the processor;
a cover overlying the display module;
memory including instructions executable by the processor;
a slot antenna formed in a gap adjacent to an interior surface of the device housing;
a conductive patch antenna formed in a cavity within the device housing, the conductive patch antenna spaced apart from the display module such that a gap is defined between the display module and the conductive patch antenna; and
antenna matching circuitry coupling the slot antenna and the conductive patch antenna, wherein electromagnetic fields induce the slot antenna and the conductive patch antenna to transmit or receive radio frequency (RF) signals over respective frequency bands.

16. The wearable computing device of claim 15, wherein the slot antenna coupled to the conductive patch antenna is configured to transmit or receive RF signals over two respective frequency bands below 3 GHz.

17. The wearable computing device of claim 15, wherein the slot antenna coupled to the conductive patch antenna is configured to transmit or receive at least one of BLUETOOTH, Wi-Fi, global positioning system (GPS), or Long-Term Evolution (LTE) communications.

18. The wearable computing device of claim 15, wherein the conductive patch antenna is a parasitic patch antenna excited by the slot antenna and configured to transmit or receive LTE low band communications.

19. The wearable computing device of claim 15, wherein slot antenna is a half-wavelength slot antenna.

20. The electronic device of claim 1, further comprising:
a printed circuit board shield coupled to the printed circuit board such that the printed circuit board shield covers a portion of the printed circuit board.

* * * * *